US008207292B2

(12) United States Patent
Nicolaou et al.

(10) Patent No.: US 8,207,292 B2
(45) Date of Patent: Jun. 26, 2012

(54) TREATMENT OF COPD, GASTRO-ESOPHAGEAL REFLUX DISEASE (GERD), FOOD ALLERGIES AND OTHER GASTROINTESTINAL CONDITIONS AND DISORDERS AMELIORATED BY PROPER HISTAMINE MANAGEMENT USING A COMBINATION OF HISTIDINE DECARBOXYLASE INHIBITORS, LRA DRUGS, ANTI-H1 AND/OR ANTI-H2 DRUGS

(76) Inventors: Michalis Nicolaou, San Diego, CA (US); Emile Loria, La Jolla, CA (US); Gaetan Terrasse, Saint-Valiere (FR); Yves Trehin, Toulouse (FR)

(*) Notice: Subject to any disclaimer, the term of this patent is extended or adjusted under 35 U.S.C. 154(b) by 1024 days.

(21) Appl. No.: 12/069,775

(22) Filed: Feb. 12, 2008

(65) Prior Publication Data
US 2008/0207530 A1 Aug. 28, 2008

Related U.S. Application Data

(60) Provisional application No. 60/889,423, filed on Feb. 12, 2007, provisional application No. 60/892,325, filed on Mar. 1, 2007, provisional application No. 60/974,685, filed on Sep. 24, 2007.

(51) Int. Cl.
*C07F 1/00* (2006.01)
*A61K 38/00* (2006.01)
(52) U.S. Cl. .................. 530/206; 530/217; 514/12.2
(58) Field of Classification Search .................. None
See application file for complete search history.

(56) References Cited

U.S. PATENT DOCUMENTS

| 4,302,458 | A | 11/1981 | Chazerain et al. |
|---|---|---|---|
| 5,256,680 | A | 10/1993 | Connor et al. |
| 5,433,948 | A | 7/1995 | Thomas et al. |
| 5,814,345 | A | 9/1998 | Beck et al. |
| 5,820,862 | A | 10/1998 | Garman et al. |
| 5,827,852 | A | 10/1998 | Russell et al. |
| 5,872,852 | A | 2/1999 | Dougherty et al. |
| 6,258,816 | B1 | 7/2001 | Singh et al. |
| 6,319,513 | B1 | 11/2001 | Dobrozsi |
| 6,455,686 | B1 | 9/2002 | McCall et al. |
| 2004/0224876 | A1* | 11/2004 | Jost-Price et al. ............. 514/11 |
| 2005/0042283 | A1* | 2/2005 | Wang ........................... 424/464 |
| 2005/0158303 | A1* | 7/2005 | Liu et al. ..................... 424/131.1 |

OTHER PUBLICATIONS

Texas GERD Institute, Center for GERD Care—Acid reflux symptoms and Treatments, See http://www.gerdcare.org/gerd-causes.htm.*
Parmar et. al. Histidine decarboxylase inhibition: a novel approach towards the development of an effective and safe gastric anti-ulcer drug. Agents and Actions, vol. 15, 5/6, 495-499 (1984).*
Engel, Nora, et al., "Experimental Evidence for Structure-Activity Features in Common Between Mammalian Histidine Decarboxylase and Ornithine Decarboxylase," *Biochem. J.,* 1996, 320:365-8 (Exhibit 1).

Urdiales, J.L. et al., "Chlorpheniramine Inhibits the Ornithine Decarboxylase Induction of Ehrlich Carcinoma Growing In Vivo." *FEBS,* Jul. 1992, 305:260-4 (Exhibit 2).
Cohen, Stanley N. et al., "Nonchromosomal Antibiotic Resistance in Bacteria: Genetic Transformation of *Escherichia coli* by R-Factor DNA," *Proc. Nat. Acad. Sci. USA,* 1972, 69:2110-4. (Exhibit 3).
Crapo, R. O. et al., "Difference in Spirometry Reference Values: A Statistical Comparison of A Mongolian and Caucasian Study," *European Respiratory Journal,* 1999, 13:606-9. (Exhibit 4).
Graham, F.L. and A.J. Van Der Eb, "A New Technique for the Assay of Infectivity of Human Adenovirus 5 DNA," *Virology,* 1973, 52:456-67. (Exhibit 5).
Southern, E. M., "Detection of Specific Sequences Among DNA Fragments Separated by Gel Electrophoresis," *Journal of Molecular Biology,* 1975, 98:503-17. (Exhibit 6).
Wigler, Michael et al., "DNA-mediated Transfer of the Adenine *Phosphoribosyltransferase locus* into Mammalian Cells," *Proc. Natl. Acad. Sci. USA,* 1979, 76:1373-6. (Exhibit 7).
Berent, Susan L. et al., "Comparison of Oligonucleotide and Long DNA Fragments as Probes in DNA and RNA Dot, Southern, Nothern, Colony and Plaque Hybridizations," *Bio Techniques,* 1985, 208-20. (Exhibit 8).
Southern, P.J. and P. Berg, "Transformation of Mammalian Cells to Antibiotic Resistance with a Bacterial Gene Under Control of the SV40 Early Region Promoter," *Journal of Molecular and Applied Genetics,* 1982, 1:327-41. (Exhibit 9).
Fasler, Stephan et al., "Antagonistic Peptides Specifically Inhibit Proliferation, Cytokine Production, CD40L Expression, and Help for IgE Synthesis by Der p. 1—Specific Human T-Cell Clones," *J. Allergy Clin Immunology,* 1998, 101:521-30 (Exhibit 19).
Hoyne, Gerard F. and Jonathan R. Lamb, "Peptide-Mediated Regulation of the Allergic Immune Response," *Immunology and Cell Biology.*1996, 74:180-6 (Exhibit 20).
van Ginkel, Frederik W. et al., "Adenoviral Gene Delivery Elicits Distinct Pulmonary-Associated T Heiper Cell Responses to the Vector and to its Transgene," *J. Immunol,* 1997, 159: 685-93 (Exhibit 21).
Hsu, Ching-Hsiang et al., "Inhibtion of Specific IgE Response in vivo By Allergen-Gene Transfer," *International Immunology,* 1996, 8:1405-11 (Exhibit 22).
Attwood, Teresa K., "The Babel of Bioinformatics," *Science,* 2000, 290:471-3 (Exhibit 23).
Whisstock, James C. and Arthur M. Lesk, "Prediction of Protein Function from Protein Sequence and Structure," *Quarterly Reviews of Biophysics,* 2003, 36:307-40 (Exhibit 24).
Verma, Inder M. and Nikunj Somia, "Gene Therapy-Promises, Problems, and Prospects," *Nature,* 1997, 389:239-42 (Exhibit 25).
Stryer, Lubert, "Levels of Structure in Protein Architecture," *Biochemistry,* 1998, 3:31-33 (Exhibit 27).
The Riverside Publishing Company, *Webster's II New Riverside University Dictionary,* 1984, 5:933 (Exhibit 28).

* cited by examiner

*Primary Examiner* — Christina Bradley
*Assistant Examiner* — Jeanette Lieb
(74) *Attorney, Agent, or Firm* — Adriano & Associates

(57) ABSTRACT

The invention provides a method for the treatment of COPD and/or gastrointestinal disease conditions ameliorated by histamine management in a subject, comprising administering to the subject an effective amount of a histidine decarboxylase inhibitor.

5 Claims, 6 Drawing Sheets

TREATMENT OF COPD, GASTRO-ESOPHAGEAL REFLUX DISEASE (GERD), FOOD ALLERGIES AND OTHER GASTROINTESTINAL CONDITIONS AND DISORDERS AMELIORATED BY PROPER HISTAMINE MANAGEMENT USING A COMBINATION OF HISTIDINE DECARBOXYLASE INHIBITORS, LRA DRUGS, ANTI-H1 AND/OR ANTI-H2 DRUGS

This application claims the priority of U.S. Ser. No. 60/889,423, filed Feb. 12, 2007, U.S. Ser. No. 60/892,325 filed Mar. 1, 2007 and U.S. Ser. No. 60/974,685 filed on Sep. 24, 2007, the contents of all of which are hereby incorporated by reference, in their entirety, into this application, and from which priority is hereby claimed.

Throughout this application various publications are referenced. The disclosures of these publications in their entireties are hereby incorporated by reference into this application in order to more fully describe the state of the art to which this invention pertains.

BACKGROUND OF THE INVENTION

Gastro-Esophageal Reflux Disease (GERD) is a common chronic disorder affecting millions of people both in the United States and worldwide. Its main symptoms, amongst others, are: heartburn, a burning sensation in the chest, occasionally a bitter taste in the mouth, cough, back pain etc.

Currently, GERD is treated with a class of drugs called proton pump inhibitors (PPI), such as, for example omeprazole and esomeprazole. Recent reports link PPI treatments as possible causes of stomach cancer, hip fracture and alkaline reflux. Additionally, PPI is not recommended for chronic patient use.

Food allergy (e.g., peanut allergy) is a growing public health concern in the United States and all over the world. Scientists are reporting an increase in food allergy over the past decade. In particular, peanut allergy among young children doubled between 1997 and 2002. Approximately 12 million Americans suffer from food allergy, with 6.9 million allergic to seafood and 3.3 million allergic to peanuts or tree nuts. It is estimated that between 150 and 200 people die annually from anaphylaxis to food; including children and young adults. Approximately 2.2 million school-aged children have food allergy. Food allergic reactions result in over 30,000 emergency room visits each year.

Food allergy is the leading cause of anaphylaxis (a severe allergic reaction) outside the hospital setting. Other causes of anaphylaxis include exercise, insect sting, latex, medication, and idiopathic reactions. Eight foods account for 90% of all reactions in the U.S.: milk, eggs, peanuts, tree nuts (walnuts, almonds, cashews, pistachios, pecans, etc.), wheat, soy, fish, and shellfish. There has been no cure for food allergy. Strict avoidance of the allergy-causing food is the only way to prevent a reaction. Food Allergy is also related to other Gastrointestinal conditions, such as increase of the intestinal permeability and GI irritation, Gastroesophagial Reflux Disease, IBD etc.

COPD (Chronic Obstructive Pulmonary Disease) is a pulmonary disease in which the lung is damaged, thus causing the patient difficulties in breathing. In COPD, the airways that carry air in and out of the lungs become partially blocked, and it becomes difficult to inhale and exhale. COPD is a major cause of death and illness throughout the world. It is the fourth leading cause of death in the U.S. and the world and causes serious, long-term disability. The number of people with COPD is currently on the rise. More than 12 million people are currently diagnosed with COPD and an additional 12 million are likely to have the disease and are undiagnosed. When COPD is severe, shortness of breath and other symptoms can get in the way of doing even the most basic tasks, such as performing light housework, taking a walk, even bathing and getting dressed. COPD develops slowly, and can worsen over time. Symptoms of COPD include constant coughing, shortness of breath, excess sputum production, feeling difficulty in breathing, inability to take a deep breath and wheezing. Currently, COPD is treated with Anticholinergic, Combination Inhaler, Corticosteroids, Inhaled Beta-2 Agonists, Inhaled Corticosteroids, Mucolytics, Oral Beta-2 Agonists and/or Theophyllines.

Anticholinergics:

Anticholinergics are used in the treatment COPD because they widen the airways by relaxing smooth muscle. They do this by blocking acetylcholine receptors. Acetylcholine is a chemical produced by the brain that causes muscle contraction, which in turn constricts airways. Anticholinergics are considered first-line therapy for COPD. The only inhaled anticholinergic agent available in the United States is ipratropium (Atrovent).

Combination Inhalers:

Recently, a new product called Advair was FDA approved for asthma but it may also be beneficial in the treatment of COPD. It combines two medications that have been on the market, salmeterol (a longer acting beta2-agonist) and fluticasone (a steroid). Many patients require both medications to help prevent asthma or COPD symptoms from worsening, but until now were only available as separate inhalers. Advair cannot be used to quickly relieve asthma or COPD symptoms, it is to be taken on a scheduled basis without regard for the symptoms the patient is having at that particular moment.

Another combination inhaler is Combivent. It contains two medications: albuterol and ipratropium. Albuterol is an inhaled beta-agonist that works in the lungs to open airways and allow for easier breathing. It does this by stimulating the beta-receptors, which are a certain type of receptor located in the lungs, which help regulate constriction and dilation of the airways. Ipratropium is an anticholinergic used in the treatment of COPD to widen the airways by relaxing and opening air passages to the lungs, making it easier to breathe.

Corticosteroids:

Corticosteroids are used to treat many health conditions. This drug class is mainly used for treating asthma, but it has been used for treating COPD. Oral corticosteroids decrease inflammation in the lungs that is associated with COPD. They may take longer to work than inhaled corticosteroids, since they have to travel through the bloodstream before they get to the lungs to work. Corticosteroids are only used in COPD patients who do not respond well to other standard therapies.

Inhaled Beta-2 Agonists:

Beta2-agonists work in a manner similar to adrenaline, opening airways and easing breathing. They work by binding with, and thus stimulating, "beta2-receptors" that line the cell walls of the lungs and the bronchioles. The effect of this stimulation is to relax smooth muscles and widen the airways. In COPD, beta2-agonists should be scheduled instead of taken on as needed basis. Possible side effects to the beta2-agonists include shakiness, rapid heartbeat, and upset stomach.

Until recently, all available beta2-agonists were ones that worked quickly but lasted for a relatively short time—about 4-6 hours. Longer-acting beta2-agonists have since been introduced. They cannot be used to quickly relieve symptoms, because there is a delay before they start working.

Currently there are two on the market: salmeterol (Serevent) and formoterol (Foradil). Longer-acting beta2-agonists are prescribed as maintenance medications which are to be taken on a scheduled basis without regard for the symptoms the patient is having at that particular moment. A short-acting beta2-agonist is best to treat acute symptoms of shortness of breath.

Inhaled Corticosteroids:

Corticosteroids suppress the body's production of substances that trigger inflammation and reduce the production of substances that maintain inflammation. This drug class is mainly used for treating asthma, but it has been used for treating COPD. Corticosteroids are only used in COPD patients who do not respond well to other standard therapies.

Mucolytics:

This class of drugs is used to thin the mucus associated with cough caused by thick mucus. Mucolytics make it easier to clear the mucus, which can be irritating and cause a cough.

Oral Beta-2 Agonists:

Oral beta2-agonists works in a similar fashion to inhaled beta2-agonists, but they may take longer to work than the inhaled formulation. Oral beta-agonists must be absorbed in the digestive tract and travel through the circulatory system before they begin working in the lungs, whereas the inhaled formulations go straight to the lungs.

Theophyllines:

Theophyllines appear to widen airways by relaxing the smooth muscles surrounding the airways. Theophylline is also used as a long-acting bronchodilator to prevent COPD symptoms. Taken orally as tablets, capsules, or liquids, theophylline is available in immediate-release and controlled-release formulations as well as injection (aminophylline).

HDC Inhibitors:

7-Amino-4,5,6-triethoxy-3-(5,6,7,8-tetrahydro-4-methoxy-6-methyl-1,3-dioxolo[4,5-g]isoquinolin-5-yl)phthalide or tritoqualine is a drug, currently formulated in 100 mg tablets and sold in pharmacies in Europe for the treatment of allergy.

Tritoqualine is an inhibitor of the enzyme histidine decarboxylase (HDC), which catalyzes histidine decarboxylation in vivo to produce histamine, an endogenous biogenic amine, plus carbon dioxide. Inhibiting histamine production in the body is proposed to ameliorate symptoms of allergy.

Leukotriene Receptor Antagonists:

Leukotriene Receptor Antagonists (LRAs), e.g., Montelukast and Zafirlukast) have been traditionally used for the treatment of asthma.

H1 Blockers and H2 Blockers:

H1 and H2 receptors are histamine receptors activated by endogenous histamine. H1 blockers (anti-H1) and H2 blockers (anti-H2) have shown some protection against gastrointestinal injury caused by the administration of Nonsteroidal Anti-inflammatory Drugs (NSAIDS). Accordingly, to avoid or alleviate this problem, NSAID compositions containing as protectants against gastrointestinal injury, an alkalizing agent together with H1 blockers, H2 blockers, beta-adrenergic agonists, or combinations thereof have been used (U.S. Pat. No. 5,071,842).

Despite the available treatments, additional and alternative therapies which are more effective to treat or prevent COPD and/or gastrointestinal conditions ameliorated by proper histamine management (e.g., GERD and/or food allergies) and pharmaceutical formulations for use in such therapies are needed.

SUMMARY OF THE INVENTION

The invention relates generally to the treatment or prevention of Gastro-Esophageal Reflux Disease (GERD), food allergy and other gastrointestinal conditions ameliorated by proper histamine management. More particularly, the invention relates to the use of combinations of histidine decarboxylase (HDC) inhibitors and anti-H1 and/or anti-H2 drugs to treat GERD and other gastrointestinal conditions ameliorated by proper histamine management. Histidine decarboxylase inhibitors, such as Tritoqualine and its isomers, play an important role for the histamine management, e.g., in the stomach. Using HDC inhibitors alone or in combination with other histamine antagonists such as anti-H1 and/or anti-H2 can significantly relieve the symptoms related to GERD and other histamine related gastrointestinal diseases compared with treatments of anti-H1 and anti-H2 alone. In fact anti-H1 alone has little effect on GERD and anti-H2 alone has been described as an inadequate treatment for GERD.

The invention provides using HDC inhibitors for the treatment or prevention of GERD and other histamine related gastrointestinal diseases. The invention further provides various forms of drug combination for the treatment of GERD and other stomach conditions ameliorated by proper histamine management. The combination includes:

1. Histidine decarboxylase inhibitor, such as Tritoqualine (or any of its isomers) and an anti-H1 drug, such as Loratadine.
2. Histidine decarboxylase inhibitor such as Tritoqualine (or any of its isomers) and an anti-H2 drug, such as Ranitidine.
3. Histidine decarboxylase inhibitor such as Tritoqualine (or any of its isomers) and an anti-H1 drug, such as Loratadine and an anti-H2 drug, such as Ranitidine.
4. Optionally, any of the above and one or more NSAIDS.

The anti-H1 drug refers to any drug that is an antagonist to the H1 receptor and the anti-H2 drug refers to any drug that is an antagonist to H2 receptor.

The invention also relates to the treatment or prevention of food allergy and other inflammatory gastrointestinal (GI) diseases using drug combinations of (a) Histidine Decarboxylase (HDC) inhibitors such as Tritoqualine and (b) Leukotriene Receptor Antagonists (LRA), such as Montelukast, Pranlukast and Zafirlukast. The invention further includes combinations of HDC inhibitors and at least one LRA with at least one anti-H1 and/or, anti-H2 drugs such as loratadine and ranitidine, respectively.

The invention further provides various forms of drug combination for the treatment of food allergy and other inflammatory gastrointestinal (GI) conditions including inflammatory bowel disease (IBD) and others, ameliorated by proper histamine management. The combination includes:

1. Histidine decarboxylase inhibitor, such as Tritoqualine (or any of its isomers) and, at least one LRA such as Montelukast, Pranlukast, and Zafirlukast.
2. Histidine decarboxylase inhibitor such as Tritoqualine (or any of its isomers), and at least one LRA such as Montelukast, and at least one Anti H2 drug, such as Ranitidine.
3. Histidine decarboxylase inhibitor such as Tritoqualine (or any of its isomers), and at least one LRA such as Montelukast, and at least one Anti H1 drug, such as Loratadine.
4. Histidine decarboxylase inhibitor such as Tritoqualine (or any of its isomers), and at least one LRA such as Montelukast, and at least one Anti H2 drug, such as Ranitidine, and at least one anti H1 drug such as Loratadine.

The invention further relates to treatment or prevention of Chronic Obstructive Pulmonary Disease (COPD) using drug combinations of histidine decarboxylase (HDC) inhibitors and anti-H1 drugs such as brompheniramine, cetirizine, fexofenadine, cyproheptadine, dexchlorpheniramine, hydroxizine, ketotifen, loratadine, mequitazine, oxotomide, mizolastine, ebastine, astemizole, carbinoxamide, alimemazine, buclizine, cyclizine hydrochloride, diphenylhydramine and doxylamine. HDC inhibitor and anti-H1 drugs may be used in combination with any one or more of existing COPD therapies including but not limited to Anticholinergics, Combination Inhaler, Corticosteroids, Inhaled Beta-2 Agonists, Inhaled Corticosteroids, Mucolytics, Oral Beta-2 Agonists and Theophyllines.

The invention further provides pharmaceutical compositions containing therapeutically effective amounts of the compounds that are useful to treat COPD, GERD, food allergies and other histamine related gastrointestinal diseases with a pharmaceutically acceptable carrier. The compounds may be combined in a single dosage form or for unit-dose or multi-dose administration. Pharmaceutical carriers suitable for administration of the compounds include any such carriers known to those skilled in the art to be suitable for the particular route of administration. The multiple active ingredients can be formulated into suitable pharmaceutical preparations such as solutions, suspensions, tablets, dispersible tablets, capsules, powders, sustained release, for oral administration or in sterile solutions or suspensions for parenteral administration, as well as transdermal patch preparation, nasal formulation and dry powder inhalers et al. The compositions are formulated into pharmaceutical compositions using techniques and procedures well known in the art.

DETAILED DESCRIPTION OF THE INVENTION

Definitions

Figure 1:
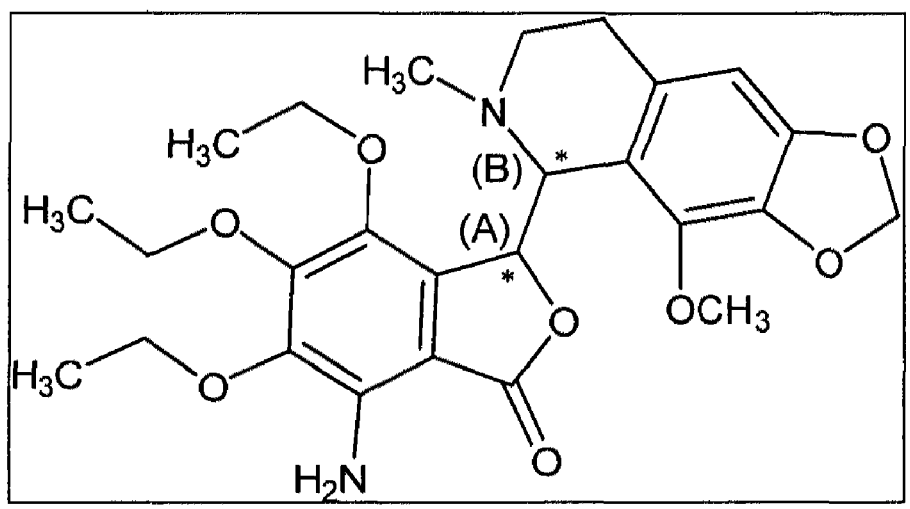
FIG. 1 illustrates the chemical formula of tritoqualine (7-Amino-4,5,6-triethoxy-3-(5,6,7,8-tetrahydro-4-methoxy-6-methyl-1,3-dioxolo[4,5-g]isoquinolin-5-yl)phthalide)

As used herein "allergy" is an abnormal or altered immunologic reaction induced by an allergen in a subject who suffers from hypersensitivity to that allergen including antibody-antigen reactions that includes immediate type hypersensitivity reactions such that when IgE molecules are crosslinked with an allergen(s), mast cells and basophils release mediators such as histamines. Examples of allergy symptoms include sinusitis, rhinitis, hives, headaches, postnasal drip, coughing, sneezing, respiratory difficulties, sore throats, allergic asthma, allergic conjunctivitis, allergic rhinitis, tightness in throat and chest, and loss of voice.

For purposes of the present invention the term "controlled release" refers to a pharmaceutical dosage form which releases one or more active pharmaceutical agents over a prolonged period of time, e.g. over a period of more than 1 hour. Controlled release (CR) components can also be referred to as sustained release (SR), prolonged release (PR), or extended release (ER). When used in association with the dissolution profiles discussed herein, the term "controlled release" refers to that portion of a dosage form made according to the present invention which delivers the compositions of the invention over a period of time e.g. greater than 1 hour. "Immediate release" refers to a dosage form which releases the compositions of the invention substantially immediately upon contact with gastric juices and will result in substantially complete dissolution within about 1 hour. Immediate release (IR) components can also be referred to as instant release. When used in association with the dissolution profiles discussed herein, the term "immediate release" refers to that portion of a dosage form made according to the present invention which delivers the compositions of the invention over a period of time less than 1 hour.

The term "derivative" means a chemically modified compound wherein the modification is considered routine by the ordinary skilled chemist, such as an ester or an amide of an acid, protecting groups, such as a benzyl group for an alcohol or thiol, and tert-butoxycarbonyl group for an amine.

The term "effective amount" means an amount of a compound or composition according to the present invention effective in producing the desired therapeutic effect.

The term "analog" means a compound which comprises a chemically modified form of a specific compound or class thereof, and which maintains the pharmaceutical and/or pharmacological activities characteristic of said compound.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluensulfonic, methanesulfonic, ethane dislfonic, oxalic, isethionic, and the like.

The phrase "pharmaceutically acceptable" is employed herein to refer to those compounds, materials, compositions; and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The term "about" when used in connection with percentages means±1-5%.

Methods of the Invention

The invention provides methods for the treatment or prevention of gastrointestinal disease conditions ameliorated by histamine management in a subject, comprising administering to the subject an effective amount of a histidine decarboxylase inhibitor. In one embodiment, the subject is given an effective amount of a histamine decarboxylase inhibitor and an anti-H1 drug. In another embodiment, the subject is given an effective amount of a histidine decarboxylase inhibitor and an anti-H2 drug. In yet another embodiment, the subject is given an effective amount of a histidine decarboxylase inhibitor, an anti-H1 drug and an anti-H2 drug. In a further embodiment, the subject may be given an effective amount of a combination of a histidine decarboxylase inhibitor, and any one or both an anti-H1 drug and an anti-H2 drug together with an NSAID.

An embodiment of the invention also provides methods for the treatment or prevention of gastrointestinal disease conditions ameliorated by histamine management in a subject comprising administering to the subject an effective amount of a HDC inhibitor in combination with an effective amount a LRA. In a further embodiment, the subject is given an effective amount of a HDC inhibitor in combination with an effective amount of a LRA and an effective amount of an anti-H1 drug. In another embodiment of the invention, the subject is given an effective amount of a HDC inhibitor in combination with an effective amount of a LRA and an effective amount of an anti-H2 drug. In a further embodiment of the invention, the subject is given an effective amount of a HDC inhibitor in combination with an effective amount of a LRA, an effective amount of an anti-H1 drug and an effective amount of an anti-H2 drug.

The gastrointestinal disease condition may be any of GERD, a food allergy, Zollinger-Ellison Syndrome, peptic ulcer, dyspepsia, allergic eosinophilic gastroenteritis, and mastocytosis with gastrointestinal symptoms.

The invention further provides methods for treatment or prevention of COPD comprising administering to the subject an effective amount of HDC inhibitor. In one embodiment, the patient is administered an effective amount of a HDC inhibitor in combination with an effective amount of an anti-H1 drug. Histidine decarboxylase inhibitors in general, as well as histamine receptor antagonists e.g. Anti-H1 drugs have never been used for the treatment of COPD. Tritoqualine (an HDC inhibitor) and Loratadine (an anti-H1 drug) were traditionally used for the treatment of allergy and primarily allergic rhinitis. The combination of Tritoqualine and Loratadine showed statistically significant effectiveness in the management of COPD when compared with the standard treatment of beta agonists, bronchodilators, steroids and oxygen. The presumed action of combining Tritoqualine and an anti-H1 drug may be by increasing the TH1 cells thus balancing the equilibrium between TH1 and TH2 cells to the detriment of TH2 cells. As a result, secretion of inflammatory cytokines such as IL4, IL5, and IL10 is reduced causing less pulmonary inflammation.

In another embodiment of the invention the patient is given HDC inhibitor in combination with any one or more of COPD therapies including but not limited to Anticholinergics, Combination Inhaler, Corticosteroids, Inhaled Beta-2 Agonists, Inhaled Corticosteroids, Mucolytics, Oral Beta-2 Agonists, Bronchodilators and Theophyllines. In a further embodiment, the patient is given HDC inhibitor and anti-H1 drug in combination with any one or more of COPD therapies including but not limited to Anticholinergics, Combination Inhaler, Corticosteroids, Inhaled Beta-2 Agonists, Inhaled Corticosteroids, Mucolytics, Oral Beta-2 Agonists, Bronchodilators and Theophyllines. In yet another embodiment of the invention, the patient is administered an effective amount of a HDC inhibitor, an anti-H1 drug and a NSAID.

Suitable examples of histidine decarboxylase inhibitors include, but are not limited to, any of Tritoqualine or an isomer thereof, alpha-fluoromethylhistidine, 3-methoxy-5,7, 3',4'-tetrahydroxyflavan, naringenin, (+)-cyanidanol-3, the dipeptide His-Phe, and 4-imidazolyl-3-amino-2-butanone, polyphenols such as catechins and related structures; these include, but are not limited to: (−)-epigallocatechin gallate, (−)-epicatechin gallate, (−)-epicatechin, (−)-epigallocatechin, and is composed of (−)-epicatechin, (−)-epigallocatechin; and other flavonoids such as O-methyl-3(+)catechin; or analogs, equivalents, isomers, pharmaceutically acceptable salts, and solvate forms of any of the above. The Tritoqualine isomer may be an SS isomer of Tritoqualine or an RR isomer of Tritoqualine. The method provides the administration of single or a combination of histidine decarboxylase inhibitors.

The dose of Tritoqualine administered to a subject may be about 200 mg/day. In another embodiment, the dose of Tritoqualine administered to a subject may be about 1 g/day. In an additional embodiment, the dose of Tritoqualine administered to a subject may be about 2 g/day. In yet another embodiment, the dose of Tritoqualine administered to a subject may be about 3 g/day. In a further embodiment, the dose of Tritoqualine administered to a subject may be about 1-5 mg/day, about 5-10 mg/day, about 10-15 mg/day, about 15-20 mg/day, about 20-25 mg/day, about 25-30 mg/day, about 30-35 mg/day, about 35-40 mg/day, about 40-45 mg/day, about 45-50 mg/day, about 50-55 mg/day, about 55-60 mg/day, about 60-65 mg/day, about 65-70 mg/day, about 70-75 mg/day, about 75-80 mg/day, about 80-85 mg/day, about 85-90 mg/day, about 90-95 mg/day, about 95-100 mg day, about 100-105 mg/day, about 105-110 mg/day, about 110-115 mg/day, about 115-120 mg/day, about 120-125 mg/day, about 125-130 mg/day, about 130-135 mg/day, about 135-140 mg/day, about 140-145 mg/day, about 145-150 mg/day, about 150-155 mg/day, about 155-160 mg/day, about 160-165 mg/day, about 165-170 mg/day, about 170-175 mg/day, about 175-180 mg/day, about 180-185 mg/day, about 185-190 mg/day, about 190-195 mg/day, about 195-200 mg/day, about 200-205 mg/day, about 205-210 mg/day, about 210-215 mg/day, about 215-220 mg/day, about 220-225 mg/day, about 225-230 mg/day, about 230-235 mg/day, about 235-240 mg/day, about 240-245 mg/day, about 245-250 mg/day, about 250-255 mg/day, about 255-260 mg/day, about 260-265 mg/day, about 265-270 mg/day, about 270-275 mg/day, about 275-280 mg/day, about 280-285 mg/day, about 285-290 mg/day, about 290-295 mg/day, about 295-300 mg/day, about 300-305 mg/day, about 305-310 mg/day, about 310-315 mg/day, about 315-320 mg/day, about 320-325 mg/day, about 325-330 mg/day, about 330-335 mg/day, about 335-340 mg/day, about 340-345 mg/day, about 345-350 mg/day, about 350-355 mg/day, about 355-360 mg/day, about 360-365 mg/day, about 365-370 mg/day, about 370-375 mg/day, about 375-380 mg/day, about 380-385 mg/day, about 385-390 mg/day, about 390-395 mg/day, about 395-400 mg/day, about 400-405 mg/day, about 405-410 mg/day, about 410-415 mg/day, about 415-420 mg/day, about 420-425 mg/day, about 425-430 mg/day, about 430-435 mg/day, about 435-440 mg/day, about 440-445 mg/day, about 445-450 mg/day, about 1 mg/day-1 g/day, about 1 mg/day-2 g/day or about 1 mg/day-3 g/day.

LRA may be used alone or in combination with steroid drugs. Suitable examples of Leukotriene Receptor Antagonists include Montelukast (Singulair), Pranlukast and Zafirlukast. The method provides the administration of single or a combination of a LRA drugs.

The dose of Montelukast (Singulair) administered to a subject may be about 10.0 mg/day. In another embodiment, the dose of Montelukast administered to a subject may be about 0.1 to 1.0 mg/day, about 1.0 to 2.0 mg/day, about 2.0 to 3.0 mg/day, about 3.0 to 4.0 mg/day, about 4.0 to 5.0 mg/day, about 5.0 to 6.0 mg/day, about 6.0 to 7.0 mg/day, about 7.0 to 8.0 mg/day, about 8.0 to 9.0 mg/day, about 9.0 to 10.0 mg/day, about 10.0 to 11.0 mg/day, about 11.0 to 12.0 mg/day, about 12.0 to 13.0 mg/day, about 13.0 to 14.0 mg/day, about 14.0 to 15.0 mg/day, about 15.0 to 16.0 mg/day, about 16.0 to 17.0 mg/day, about 17.0 to 18.0 mg/day, about 18.0 to 19.0 mg/day, about 19.0 to 20.0 mg/day, about 20.0 to 21.0 mg/day, about 21.0 to 22.0 mg/day, about 22.0 to 23.0 mg/day, about 23.0 to 24.0 mg/day, about 24.0 to 25.0 mg/day, about 25.0 to 26.0 mg/day, about 26.0 to 27.0 mg/day, about 27.0 to 28.0 mg/day, about 28.0 to 29.0 mg/day, about 29.0 to 30.0 mg/day, about 30.0 to 31.0 mg/day, about 31.0 to 32.0 mg/day, about 32.0 to 33.0 mg/day, about 33.0 to 34.0 mg/day, about 34.0 to 35.0 mg/day or about 1 mg/day to 35 mg/day.

In accordance with the practice of the invention, suitable examples of anti-H1 drugs includes, but are limited to, any of brompheniramine, cetirizine, fexofenadine, cyproheptadine, dexchlorpheniramine, hydroxizine, ketotifen, Loratadine, mequitazine, oxotomide, mizolastine, ebastine, astemizole, carbinoxamide, alimemazine, buclizine, cyclizine hydrochloride, doxylamine, mepyramine, antazoline, diphenhydramine, carbinoxamine, clemastine, dimenhydrinate, pheniramine, chlorphenamine, triprolidine, chlorcyclizine, hydroxyzine, meclizine, promethazine, and azatadine or analogs, equivalents, isomers, pharmaceutically acceptable salts, and solvate forms thereof. The method provides the administration of single or a combination of anti-H1 drugs.

The dose of loratadine administered to a subject may be about 10.0 mg/day. In another embodiment, the dose of loratadine administered to a subject may be about 0.1 to 1.0 mg/day, about 1.0 to 2.0 mg/day, about 2.0 to 3.0 mg/day, about 3.0 to 4.0 mg/day, about 4.0 to 5.0 mg/day, about 5.0 to 6.0 mg/day, about 6.0 to 7.0 mg/day, about 7.0 to 8.0 mg/day, about 8.0 to 9.0 mg/day, about 9.0 to 10.0 mg/day, about 10.0 to 11.0 mg/day, about 11.0 to 12.0 mg/day, about 12.0 to 13.0 mg/day, about 13.0 to 14.0 mg/day, about 14.0 to 15.0 mg/day, about 15.0 to 16.0 mg/day, about 16.0 to 17.0 mg/day, about 17.0 to 18.0 mg/day, about 18.0 to 19.0 mg/day, about 19.0 to 20.0 mg/day, about 20.0 to 21.0 mg/day, about 21.0 to 22.0 mg/day, about 22.0 to 23.0 mg/day, about 23.0 to 24.0 mg/day, about 24.0 to 25.0 mg/day, about 25.0 to 26.0 mg/day, about 26.0 to 27.0 mg/day, about 27.0 to 28.0 mg/day, about 28.0 to 29.0 mg/day, about 29.0 to 30.0 mg/day, about 30.0 to 31.0 mg/day, about 31.0 to 32.0 mg/day, about 32.0 to 33.0 mg/day, about 33.0 to 34.0 mg/day, about 34.0 to 35.0 mg/day or about 1 mg/day to about 35 mg/day.

The dose of cetirizine administered to a subject may be about 10 mg/day. In another embodiment, the dose of cetirizine administered to a subject may be about 0.1 to 0.5 mg/day, about 0.5 to 1.0 mg/day, about 1.0 to 1.5 mg/day, about 1.5 to 2.0 mg/day, about 2.0 to 2.5 mg/day, about 2.5 to 3.0 mg/day, about 3.0 to 3.5 mg/day, about 3.5 to 4.0 mg/day, about 4.0 to 4.5 mg/day, about 4.5 to 5.0 mg/day, about 5.0 to 5.5 mg/day, about 5.5 to 6.0 mg/day, about 6.0 to 6.5 mg/day, about 6.5 to 7.0 mg/day, about 7.0 to 7.5 mg/day, about 7.5 to 8.0 mg/day, about 8.5 to 9.0 mg/day, about 9.0 to 9.5 mg/day, about 9.5 to 10.0 mg/day, about 10.5 to 11.0 mg/day, about 11.0 to 11.5 mg/day, about 11.5 to 12.0 mg/day, about 12.0 to 12.5 mg/day, about 12.5 to 13.0 mg/day, about 13.0 to 13.5 mg/day, about 13.5 to 14.0 mg/day, about 14.0 to 14.5 mg/day, about 14.5 to 15.0 mg/day, about 15.0 to 15.5 mg/day, about 15.5 to 16.0 mg/day, about 16.0 to 16.5 mg/day, about 16.5 to 17.0 mg/day, about 17.0 to 17.5 mg/day, about 17.5 to 18.0 mg/day, about 18.5 to 19.0 mg/day, about 19.0 to 19.5 mg/day, about 19.5 to 20.0 mg/day, about 20.5 to 21.0 mg/day, about 21.0 to 21.5 mg/day, about 21.5 to 22.0 mg/day, about 22.0 to 22.5 mg/day, about 22.5 to 23.0 mg/day, about 23.0 to 23.5 mg/day, about 23.5 to 24.0 mg/day, about 24.0 to 24.5 mg/day, about 24.5 to 25.0 mg/day, about 25.0 to 25.5 mg/day, about 25.5 to 26.0 mg/day, about 26.0 to 26.5 mg/day, about 26.5 to 27.0 mg/day, about 27.0 to 27.5 mg/day, about 27.5 to 28.0 mg/day, about 28.5 to 29.0 mg/day, about 29.0 to 29.5 mg/day, about 29.5 to 30.0 mg/day or about 0.5 mg/day to 30.0 mg/day.

The dose of fexofenadine administered to a subject may be about 120.0 mg/day. In another embodiment, the dose of fexofenadine administered to a subject may be about 1.0 to 30.0 mg/day, about 30.0 to 50.0 mg/day, about 50.0 to about 70.0 mg/day, about 70.0 to 90.0 mg/day, about 90.0 to 110.0 mg/day, about 110.0 to 130.0 mg/day, about 130.0 to 150.0 mg/day, about 150.0 to 170.0 mg/day, about 170.0 to 190.0 mg/day, about 190.0 to 210.0 mg/day, about 210.0 to 230.0 mg/day, about 230.0 to 250.0 mg/day, about 250.0 to 270.0 mg/day, about 270.0 to 290.0 mg/day, about 290.0 to 310.0 mg/day, about 310.0 to 330.0 mg/day, about 330.0 to 350.0 mg/day, about 350.0 to 370.0 mg/day, about 370.0 to 390.0 mg/day, about 390.0 to 410.0 mg/day, about 410.0 to 430.0 mg/day, about 430.0 to 450.0 mg/day, about 450.0 to 470.0 mg/day, about 470.0 to 490.0 mg/day, about 490.0 to 510.0 mg/day or about 1 mg/day to 510 mg/day.

Suitable examples of anti-H2 drugs include, but are not limited to, any of ranitidine, cimetidine, famotidine, and nizatidine and/or analogs, equivalents, isomers, pharmaceutically acceptable salts, and solvate forms thereof. The method provides the administration of a single or combination of anti-H2 drugs.

The dose of ranitidine administered to a subject may be about 150 mg/day. In another embodiment, the dose of ranitidine administered to a subject may be about 1.0 to 20.0 mg/ml, about 20.0 to 40.0 mg/ml, about 40.0 to 60.0 mg/ml, about 60.0 to 80.0 mg/ml, about 80.0 to 100.0 mg/ml, about 100.0 to 120.0 mg/ml, about 120.0 to 140.0 mg/ml, about 140.0 to 160.0 mg/ml, about 160.0 to 180.0 mg/ml, about 180.0 to 200.0 mg/ml, about 200.0 to 220.0 mg/ml, about 220.0 to 240.0 mg/ml, about 240.0 to 260.0 mg/ml, about 260.0 to 280.0 mg/ml, about 280.0 to 300.0 mg/ml, about 300.0 to 320.0 mg/ml, about 320.0 to 340.0 mg/ml, about 340.0 to 360.0 mg/ml, about 360.0 to 380.0 mg/ml, about 380.0 to 400.0 mg/ml, about 400.0 to 420.0 mg/ml, about 420.0 to 440.0 mg/ml, about 440.0 to 460.0 mg/ml, about 460.0 to 480.0 mg/ml, about 480.0 to 500.0 mg/ml, about 500.0 to 520.0 mg/ml, about 520.0 to 540.0 mg/ml, about 540.0 to 560.0 mg/ml, about 560.0 to 580.0 mg/ml, about 580.0 to 600.0 mg/ml, about 600.0 to 620.0 mg/ml, about 620.0 to 640.0 mg/ml, about 640.0 to 660.0 mg/ml, about 660.0 to 680.0 mg/ml, about 680.0 to 700.0 mg/ml, about 700.0 to 720.0 mg/ml, about 720.0 to 740.0 mg/ml, about 740.0 to 760.0 mg/ml, about 760.0 to 780.0 mg/ml, about 780.0 to 800.0 mg/ml, about 800.0 to 820.0 mg/ml, about 820.0 to 840.0 mg/ml, about 840.0 to 860.0 mg/ml, about 860.0 to 880.0 mg/ml, about 880.0 to 900.0 mg/ml or about 1 mg/ml to about 900 mg/ml.

NSAIDs include, but are not limited to acetyl salicylic acid (Aspirin), Amoxiprin, Benorilate, choline magnesium salicylate, diflunisal, Faislamine, Methyl salicylate, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors, meloxicam, tramadol, Aceclofenac, Acemetacin, Bromfenac, Etodolac, Indometacin, Nabumetone, Sulindac, Tolmetin, Ibuprofen, Carprofen, Fenbufen, Loxoprofen, Oxaprozin, Tiaprofenic acid, Suprofen, Mefenamic acid, Meclofenamicacid, Phenylbutazone, Azapropazone, Metamizole, Oxyphenbutazone, Sulfinpyrazone, Meloxicam, Piroxicam, Lornoxicam and Tenoxicam. In a preferred embodiment, NSAIDs include Aspirin, Meloxicam, Ibuprofen, Naproxen. The method provides the administration of a single or combination of NSAIDS.

In accordance with the practice of the invention, for each given daily dose of a drug, or combination of drugs, listed above, the given dose may be administered once a day or multiple times a day. For example, ½ of the given dose may be administered twice a day. In another embodiment of the invention, ⅓ of the given dose may be administered 3 times a day. In a further embodiment of the invention, ¼ of the given dose may be administered 4 times a day. In yet another embodiment of the invention, ⅕ of the given dose may be administered 5 times a day. In yet another embodiment of the invention, ⅙ of the given dose may be administered 6 times a day. In yet another embodiment of the invention, ⅐ of the given dose may be administered times a day. In yet another embodiment of the invention, ⅛ of the given dose may be is administered 8 times a day. In yet another embodiment of the invention, ⅑ of the given dose may be administered 9 times a day. In yet another embodiment of the invention, ⅒ of the given dose may be administered 10 times a day.

Additionally, for each given daily dose of a drug listed above, various fractions of the given dose may be administered to the subject at multiple times during the day, with the sum of the various fractions adding up to the given dose. For example, the amount of the fraction of the given dose administered to the subject at a given time may be any of ½ of the given dose, ⅓ of the given dose, ¼ of the given dose, ⅕ of the given dose, ⅙ of the given dose, ⅐ of the given dose, ⅛ of the given dose, ⅑ of the given dose, or ⅒ of the given dose. In another embodiment of the invention, the fraction of the given dose that is administered, and the total number of times the drug is administered can vary by day. In a further embodiment of the invention, the time of day the given dose or fraction of the given dose is administered can vary by day.

Dosage of the therapeutic agent(s) is dependant upon many factors including, but not limited to, the type of tissue affected, the type of disease being treated, the severity of the disease, a subject's health and response to the treatment with the agents. Accordingly, dosages of the agents can vary depending on each subject and the mode of administration.

In accordance with the practice of the invention, the subject may be a mammal. In other embodiments of the invention, the subject may be any of human, monkey, ape, dog, cat, cow, horse, rabbit, mouse, or rat.

In accordance with the practice of the invention, the administration of a given drug may be effected locally or systemically. Additionally, the route of administration of a given drug may be any of topical, enteral or parenteral. In other embodiments of the invention, the route of administration of a given drug may be any of rectal, intercisternal, bucal, intramuscular, intrasternal, intracutaneous, intrasynovial, intravenous, intraperitoneal, intraocular, periostal, intra-articular injection, infusion, oral, inhalation, subcutaneous, implantable pump, continuous infusion, gene therapy, intranasal, intrathecal, intracerebroventricular, transdermal, or by injection.

In accord with the practice of the invention, the route of administration of a given drug can vary during a course of treatment, or during a given day. For example, if a given drug is administered in conjunction with one or more additional drugs, each additional drug may be administered by identical or different routes compared to the other drugs.

The combination of a histidine decarboxylase inhibitor with anti-H1 and/or anti-H2 drugs and/or a LRA drug can be prepared in a single dosage form in oral, parenteral, topical, and other systemic dosage forms.

The administration of a given drug to a subject can be performed daily, weekly, monthly, every other month, quarterly, or any other schedule of administration as a single dose administration, in multiple doses, or in continuous dose form. Additionally, a given drug is administered to a subject intermittently, or at a gradual, continuous, constant, or controlled rate to a subject.

In accord with the practice of the invention, if other drugs are being administered in addition to the agents of the invention, the timing of administration of each drug may be identical to or different from the timing of the other drugs.

The agents of the invention (also referred to herein as therapeutic agents, compositions of the invention, e.g., anti-GERD compositions or compositions for the treatment of GERD or compositions for treatment of food allergies or anti-food allergy compositions or anti-COPD compositions or compositions for the treatment of COPD) may be administered either concomitantly, e.g., as an admixture, separately but simultaneously or concurrently or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second, and or third agent.

The agents of the invention may be administered alone or in combination with other therapeutic agents. Components of the combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In accordance with the practice of the invention, the subject may have any one or more of the following: 1) a history of GERD; 2) a history of allergies (for example food allergies); 3) a history of COPD; 4) previous unsatisfactory treatment with an anti-H1 and/or anti-H2 drug; 5) previously unsatisfactory treatment with existing COPD therapies; 6) previous unsatisfactory treatment with proton pump inhibitors (PPI); 7) previous diagnosis of GERD and concurrent symptoms of allergy; and/or 8) previous unsatisfactory treatment with cromoglycate.

In one embodiment, the subject may suffer from COPD or GERD (or any of the gastrointestinal disorders or diseases disclosed herein) but does not exhibit allergy symptoms which include any one or more of allergic asthma, allergic conjunctivitis, and allergic rhinitis.

For example, the allergy may be confirmed with two positive prick tests for the same allergen or set of allergens. The allergens may be any of *Dermatophagoid Ptermonysisnus, Demathophagoid Farinae*, cat dander, dog dander, food allergens, fungal proteins, and pollen proteins. Additionally, the food allergen may be any of wheat, egg, soy, potato, peanut, and/or tomato proteins. The fungal protein may be any of a protein from a species in the *alternaria* genus, a protein from a species in the *mucor* genus, and a protein from a species in the *aspergillus* genus. The pollen protein may be any of pollen of birch tree, pollen of cypress tree, pollen of *Quercus* tree, pollen of *lolium perenne*, and pollen of ray grass.

Compositions of the Invention

The present invention provides pharmaceutical compositions, dosage forms or formulations (e.g., anti-GERD or anti-COPD compositions) containing two or more active agents of the invention chosen from among: (i) an antihistamine compound(s), and/or (ii) an inhibitor(s) of histamine synthesis; and optionally one or more NSAIDs. The present invention also provides pharmaceutical compositions, dosage forms or formulations (e.g., compositions for treatment of food allergies) containing two or more active agents of the invention chosen from among: (i) an antihistamine compound(s), and/ or (ii) a Leukotriene Receptor Antagonist (LRA) drug(s) and/ or (ii) an inhibitor(s) of histamine synthesis; and optionally one or more NSAIDs. Said agents of the invention may be associated in said composition with a pharmaceutically acceptable carrier or vehicle. Pharmaceutically acceptable carrier or vehicle refers to a non-toxic solid, semisolid (also referred to herein as softgel) or liquid filler, diluent, encapsulating material or formulation auxiliary of any type. The invention also provides methods for treating or preventing of GERD, COPD and food allergies (or other gastrointestinal diseases or disorders) using said compositions.

H1 antagonists include, but are not limited to, any or a combination of, brompheniramine, cetirizine, levocetirizine, fexofenadine, cyproheptadine, dexchlorpheniramine, hydroxizine, ketotifen, loratadine, mequitazine, oxotomide, mizolastine, ebastine, astemizole, carbinoxamide, alimemazine, buclizine, cyclizine hydrochloride, doxylamine, mepyramine, antazoline, diphenhydramine, carbinoxamine, clemastine, dimenhydrinate, pheniramine, chlorphenamine, triprolidine, chlorcyclizine, hydroxyzine, meclizine, promethazine and azatadine and/or analogs, equivalents, isomers, salts, and solvate forms thereof. Another suitable example of an antihistamine compound is an H2 antagonist (anti-H2). H2 antagonists include, but are not limited ranitidine, cimetidine, famotidine, and nizatidine and/or analogs, equivalents, isomers, salts, and solvate forms thereof.

Inhibitors of histamine synthesis include, but are not limited to, an inhibitor of histidine decarboxylase such as tritoqualine, an isomer thereof, alpha-fluoromethylhistidine, 3-methoxy-5,7,3',4'-tetrahydroxyflavan, naringenin, (+)-cyanidanol-3, the dipeptide His-Phe, 4-imidazolyl-3-amino-2-butanone, and catechins such as, epigallocatechin gallate.

A first preferred embodiment of an anti-GERD pharmaceutical composition, anti-COPD pharmaceutical composition or an anti-food allergy pharmaceutical composition, according to the invention contains at least one antihistamine compound, in a pharmaceutically acceptable vehicle. A suitable example of an antihistamine compound is an H1 antagonist (anti-H1).

In a further embodiment, the anti-GERD, anti-COPD or anti-food allergy pharmaceutical composition comprises an antihistamine compound and an inhibitor of histamine synthesis. For example, in a particular embodiment, the inhibitor of histamine synthesis is tritoqualine and the antihistamine compound is an H1 antagonist.

A preferred embodiment of a pharmaceutical composition for treatment of food allergies according to the invention contains at least one LRA drug, in a pharmaceutically acceptable vehicle. Suitable examples of LRA drugs include, but are not limited to, Montelukast, Pranlukast and Zafirlukast and/or analogs, equivalents, isomers, salts, and solvate forms thereof.

In a further embodiment, a pharmaceutical composition for treatment of food allergies comprises an inhibitor of histamine synthesis and LRA drugs. Suitable examples of LRA drugs include, but are not limited to, Montelukast, Pranlukast and Zafirlukast and/or analogs, equivalents, isomers, salts, and solvate forms thereof. In a particular embodiment, the inhibitor of histamine synthesis is tritoqualine. In another particular embodiment, the inhibitor of histamine synthesis is tritoqualine and the LRA is Montelukast.

In an additional embodiment, a pharmaceutical composition for treatment of food allergies comprises an inhibitor of histamine synthesis, LRA drugs and an antihistamine compound. An inhibitor of histamine synthesis may be tritoqualine. A suitable LRA drug may be Montelukast, Pranlukast and/or Zafirlukast. In one embodiment, the LRA drug is Montelukast. A suitable example of an antihistamine compound is an H1 antagonist (anti-H1).

The present invention also provides pharmaceutical compositions (e.g., anti-GERD compositions, anti-COPD and/or anti-food allergy compositions) comprising a solid or liquid dosage form of tritoqualine and a plurality of particles which permit the formulation of solid or liquid dosage form of tritoqualine. The particles comprise, but are not limited to, excipients disclosed herein below, e.g., typical excipients for softgels.

In one embodiment, the solid or liquid dosage form of tritoqualine composition further comprises an H1 antagonist. In another embodiment, the solid or liquid dosage form of the tritoqualine composition further comprises an H2 antagonist. In yet another embodiment, the solid or liquid dosage form of tritoqualine further comprises both an H1 and an H2 antagonist. In a further embodiment, the solid or liquid dosage form of the tritoqualine composition further comprises a LRA drug. In an additional embodiment, the solid or liquid dosage form of the tritoqualine composition further comprises a LRA drug and an anti-H1 drug. Another embodiment of the solid or liquid dosage form of the tritoqualine composition further comprises a LRA drug, an anti-H1 drug and an anti-H2 drug.

In one aspect, the present invention provides a pharmaceutical composition for the treatment of GERD, COPD and/or food allergies comprising a solid or liquid dosage form of tritoqualine, wherein the composition is an administrable formulation that allows resorption of the tritoqualine into a subject. In one embodiment, the administrable formulation can be, e.g., an inhalant or a topically administrable formulation such as an ointment or cream.

A particular form of implementation of the invention consists of an anti-GERD or anti-COPD pharmaceutical composition comprising at least one antihistamine compound and at least one inhibitor of histamine synthesis, associated with a pharmaceutically acceptable vehicle.

A particular form of implementation of the invention consists of a pharmaceutical composition for treatment of food allergies comprising at least one LRA, at least one antihistamine compound and at least one inhibitor of histamine synthesis, associated with a pharmaceutically acceptable vehicle.

In one embodiment, the invention provides an anti-GERD or anti-COPD pharmaceutical composition comprising a histidine decarboxylase inhibitor (e.g., tritoqualine), an NSAID and optionally an anti-H2 drug together with a pharmaceutically acceptable vehicle to protect against gastrointestinal injury.

An embodiment of the invention provides a pharmaceutical composition for treatment of food allergies comprising a histidine decarboxylase inhibitor, e.g., tritoqualine, and an NSAID.

Anti-H1 and anti-H2 drugs are present in the various compositions of the invention in a proportion of the order of 0.1 to 2000 mg.

In the case of a composition according to the invention containing an antihistamine compound (for example, anti-H1, anti-H2) and an inhibitor of histamine synthesis, these compounds are present in a proportion of the order of:
- 0.5 to 2000 mg of anti H2 compound (when used),
- 0.1 to 2000 mg of anti-H1 compound (when used)
- 0.10 to 3000 mg of an inhibitor of histidine decarboxylase such as tritoqualine.

In the case of a composition according to the invention containing an antihistamine compound (for example, anti-H1, anti-H2), an LRA drug and an inhibitor of histamine synthesis, these compounds are present in a proportion of the order of:
- 0.5 to 2000 mg of anti H2 compound (when used),
- 0.1 to 2000 mg of anti-H1 compound (when used)
- 0.1 to 2000 mg of a LRA drug (when used)
- 0.10 to 3000 mg of an inhibitor of histidine decarboxylase such as tritoqualine.

Further, the composition of the invention can be pegylated, phosphorylated, esterified, derivatize with amino acids and/or peptides, to improve solubility for both formulation and bioavailability. Additionally, lipid derivatization and other lipophile derivatization can be used to improve mucosal permeability, absorption and formulation of the compositions of the invention in oily vehicles.

Dosage Forms

Dosage forms can be made according to well known methods in the art. Some preferred methods are described below.

The pharmaceutical compositions of the invention may be formulated as solid dosage forms, such as capsules, pills, softgels, tablets, caplets, troches, wafer, sprinkle, chewing gum or the like, for oral administration. The pharmaceutical compositions of the invention may also be formulated as liquid dosage forms such as elixir, suspension or syrup.

The pharmaceutical compositions of the invention may also be presented in a dosage form for transdermal application, for example an ointment for children, a form for oral administration, for example a slow release product, or in gastro-resistant tablet form or gum form. They may also be in spray, bronchial form or eye lotion form, or other galenic forms with programmed mucosal and secondarily per os disintegration.

Therefore the different pharmaceutical compositions of the invention can be administered by several routes chosen in accordance with the patient's pathological profile and age. For children, the patch form, syrup form or tablets to be dissolved in the mouth. The other forms, eye lotion or injection may also be used. In adults all galenic forms (also known as dosage forms) can be contemplated.

The advantage of a coupled or combined galenic form also provides simplicity of treatment, patient compliance with the simplified treatment and therefore a more successful outcome.

The pharmaceutical compositions of the present invention may be mixed with pharmaceutically acceptable carriers, binders, diluents, adjuvants, excipients, or vehicles, such as preserving agents, fillers, polymers, disintegrating agents, glidants, wetting agents, emulsifying agents, suspending agents, sweetening agents, flavoring agents, perfuming agents, lubricating agents, acidifying agents, coloring agent, dyes, preservatives and dispensing agents, or compounds of a similar nature depending on the nature of the mode of administration and dosage forms. Such ingredients, including pharmaceutically acceptable carriers and excipients that may be used to formulate oral dosage forms, are described in the Handbook of Pharmaceutical Excipients, American Pharmaceutical Association (1986), incorporated herein by reference in its entirety.

Pharmaceutically acceptable carriers are generally non-toxic to recipients at the dosages and concentrations employed and are compatible with other ingredients of the formulation. Examples of pharmaceutically acceptable carriers include water, saline, Ringer's solution, dextrose solution, ethanol, polyols, vegetable oils, fats, ethyl oleate, liposomes, waxes polymers, including gel forming and non-gel forming polymers, and suitable mixtures thereof. The carrier may contain minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulin; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG. Preferably the carrier is a parenteral carrier, more preferably a solution that is isotonic with the blood of the recipient.

Examples of binders include, but are not limited to, microcrystalline cellulose and cellulose derivatives, gum tragacanth, glucose solution, acacia mucilage, gelatin solution, molasses, polyinylpyrrolidine, povidone, crospovidones, sucrose and starch paste.

Examples of diluents include, but are not limited to, lactose, sucrose, starch, kaolin, salt, mannitol and dicalcium phosphate.

Examples of excipients include, but are not limited to, starch, surfactants, lipophilic vehicles, hydrophobic vehicles, pregelatinized starch, Avicel, lactose, milk sugar, sodium citrate, calcium carbonate, dicalcium phosphate, and lake blend purple. Typical excipients for dosage forms such as a softgel include gelatin for the capsule and oils such as soy oil, rice bran oil, canola oil, olive oil, corn oil, and other similar oils; glycerol, polyethylene glycol liquids, vitamin E TPGS as a surfactant and absorption enhancer (Softgels: Manufacturing Considerations; Wilkinson P, Foo Sog Hom, Special Drug Delivery Systems; Drugs and the Pharmaceutical Sciences Vol 41 Praveen Tyle Editor, Marcel Dekker 1990, 409-449; Pharmaceutical Dosage Forms and Drug Delivery by Ansel, Popovich and Allen 1995, Williams and Wilkins, Chapter 5 pp 155-225). Tritoqualine and anti H1 may form either a solution in a selected oil vehicle or a suspension of fine particles (comprising any of the excipients disclosed herein, e.g., typical excipients for softgels).

Examples of disintegrating agents include, but are not limited to, complex silicates, crosscarmellose sodium, sodium starch glycolate, alginic acid, corn starch, potato starch, bentonite, methylcellulose, agar and carboxymethylcellulose.

Examples of glidants include, but are not limited to, colloidal silicon dioxide, talc, corn starch.

Examples of wetting agents include, but are not limited to, propylene glycol monostearate, sorbitan monooleate, diethylene glycol monolaurate and polyoxyethylene laural ether.

Examples of sweetening agents include, but are not limited to, sucrose, lactose, mannitol and artificial sweetening agents such as saccharin, and any number of spray dried flavors.

Examples of flavoring agents include, but are not limited to, natural flavors extracted from plants such as fruits and synthetic blends of compounds which produce a pleasant sensation, such as, but not limited to peppermint and methyl salicylate.

Examples of lubricants include magnesium or calcium stearate, sodium lauryl sulphate, talc, starch, *lycopodium* and stearic acid as well as high molecular weight polyethylene glycols.

Examples of coloring agents include, but are not limited to, any of the approved certified water soluble FD and C dyes, mixtures thereof; and water insoluble FD and C dyes suspended on alumina hydrate.

The artisan of ordinary skill in the art will recognize that many different ingredients can be used in formulations according to the present invention and the list provided herein is not exhaustive.

Matrix Based Dosage Forms

Dosage forms according to one embodiment of the present invention may be in the form of coated or uncoated matrices. The term matrix, as used herein, is given its well known meaning in the pharmaceutical arts as a solid material having an active agent (e.g., the components of the compositions of the invention) of the invention incorporated therein. Upon exposure to a dissolution media, channels are formed in the solid material so that the active agent can escape.

The skilled artisan will appreciate that the matrix material can be chosen from a wide variety of materials which can provide the desired dissolution profiles. Materials can include, for example, one or more gel forming polymers such as polyvinyl alcohol, cellulose ethers including, for example, hydroxypropylalkyl celluloses such as hydroxypropyl cellulose, hypromellose, prop-2-enoic acid, hydroxypropyl methyl cellulose, hydroxyalkyl celluloses such as hydroxypropyl cellulose, natural or synthetic gums such as guar gum, xanthum gum, and alginates, as well as ethyl cellulose, polyvinyl pyrrolidone, fats, waxes, polycarboxylic acids or esters such as the Carbopol R series of polymers, methacrylic acid copolymers, and methacrylate polymers.

In addition to the above-mentioned ingredients, a controlled release matrix may also contain suitable quantities of other materials, for example, diluents, lubricants, binders, granulating aids, colorants, flavorants, and glidants that are conventional in the pharmaceutical arts. The quantities of these additional materials should be sufficient to provide the desired effect to the desired formulation. A controlled release matrix incorporating particles may also contain suitable quantities of these other materials such as diluents, lubricants, binders, granulating aids, colorants, flavorants, and glidants that are conventional in the pharmaceutical arts in amounts up to about 75% by weight of the particulate, if desired.

Methods of making matrix dosages are well known in the art and any known method of making such dosages which yields the desired immediate release and controlled release dissolution profiles can be used. One such method involves the mixture of the compositions of the invention with a solid polymeric material and one or more pharmaceutically acceptable excipients which can then be blended and compressed in controlled release tablet cores. Such tablet cores can be used for further processing as bi-layer or multilayer tablets, press coated tablets, or film coated tablets.

In addition, the formulation of respective release components can occur by appropriate granulation methods as is well known in the art. In wet granulation, solutions of the binding agent can be added with stirring to the mixed powders. The powder mass can be wetted with the binding solution until the mass has the consistency of damp snow or brown sugar. The wet granulated material can be forced through a sieving device. Moist material from the milling step can be dried by placing it in a temperature controlled container. After drying, the granulated material can be reduced in particle size by passing it through a sieving device. Lubricant can be added, and the final blend can then be compressed into a matrix dosage form such as a matrix tablet.

In fluid-bed granulation, particles of inert material and/or active agent (e.g., the components of the compositions of the invention) can be suspended in a vertical column with a rising air stream. While the particles are suspended, a common granulating material in solution can be sprayed into the column. There will be a gradual particle buildup under a controlled set of conditions resulting in tablet granulation. Following drying and the addition of lubricant, the granulated material will be ready for compression.

In dry-granulation, the active agent (e.g., the components of the compositions of the invention), binder, diluent, and lubricant can be blended and compressed into tablets. The compressed large tablets can be comminuted through the desirable mesh screen by sieving equipment. Additional lubricant can be added to the granulated material and blended gently. The material can then be compressed into tablets.

Particle Based Dosage Forms

Immediate Release and Controlled Release Particles

Dosage forms according to another embodiment of the present invention may be in the form of coated or uncoated immediate release/controlled release dosage forms. The immediate release/controlled release dosage forms of the present invention can take the form of pharmaceutical particles. The dosage forms can include immediate release particles in combination with controlled release particles in a ratio sufficient to deliver the desired dosages of active agents (e.g., the components of the compositions of the invention). The controlled release particles can be produced by coating the immediate release particles with an enteric coat.

The particles can be produced according to any of a number of well known methods for making particles. The immediate release particles can comprise the active agent combination (the compositions of the invention) and a disintegrant. Suitable disintegrants can include, for example, starch, low-substitution hydroxypropyl cellulose, croscarmellose sodium, calcium carboxymethyl cellulose, hydroxypropyl starch, and microcrystalline cellulose.

In addition to the above-mentioned ingredients, a controlled release matrix may also contain suitable quantities of other materials, for example, diluents, lubricants, binders, granulating aids, colorants, flavorants, and glidants that are conventional in the pharmaceutical arts. The quantities of these additional materials should be sufficient to provide the desired effect to the desired formulation. A controlled release matrix incorporating particles may also contain suitable quantities of these other materials such as diluents, lubricants, binders, granulating aids, colorants, flavorants, and glidants that are conventional in the pharmaceutical arts in amounts up to about 75% by weight of the particulate, if desired.

Particles can assume any standard structure known in the pharmaceutical arts. Such structures can include, for example, matrix particles, non-pareil cores having a drug layer and active or inactive cores having multiple layers thereon. A controlled release coating can be added to any of these structures to create a controlled release particle.

The term particle as used herein means a granule having a diameter of between about 0.01 mm and about 5.0 mm, preferably between about 0.1 mm and about 2.5 mm, and more preferably between about 0.5 mm and about 2 mm. The skilled artisan will appreciate that particles according to the present invention can be any geometrical shape within this size range and so long as the mean for a statistical distribution of particles falls within the particle sizes enumerated above, they will be considered to fall within the contemplated scope of the present invention.

The release of the therapeutically active agent (e.g., the components of the compositions of the invention) from the controlled release formulation of the present invention can be further influenced, i.e., adjusted to a desired rate, by the addition of one or more release-modifying agents. The release-modifying agent may be organic or inorganic and include materials that can be dissolved, extracted, or leached from the coating in the environment of use. The pore-formers may comprise one or more hydrophilic materials such as hydroxypropyl methylcellulose. The release-modifying agent may also comprise a semi-permeable polymer. In certain preferred embodiments, the release-modifying agent is selected from hydroxypropyl methylcellulose, lactose, metal stearates, and mixtures thereof.

The controlled release particles of the present invention can slowly release the compositions of the invention when ingested. The controlled release profile of the formulations of the present invention can be altered, for example, by increasing or decreasing the thickness of a retardant coating, i.e., by varying the amount of overcoating. The resultant solid controlled release particles may thereafter be placed in a gelatin capsule in an amount sufficient to provide an effective controlled release dose when ingested and contacted by an environmental fluid, e.g., gastric fluid, intestinal fluid or dissolution media.

The dosage forms of the invention may be coated (e.g., film coated or enterically coated) as known by those of skill in the art. For example, the composition can be formulated in an enteric coating that maintains its integrity in the stomach and releases the active compound in the intestine.

Examples of enteric-coatings include, but are not limited to, phenylsalicylate, fatty acids, fats, waxes, shellac, ammoniated shellac and cellulose acetate phthalates. Film coatings include, but are not limited to, hydroxyethylcellulose, sodium carboxymethylcellulose, polyethylene glycol 4000 and cellulose acetate phthalate.

In one example, the dosage forms e.g, particles of the invention as described above, may be overcoated with an aqueous dispersion of a hydrophobic or hydrophilic material to modify the release profile. The aqueous dispersion of hydrophobic material preferably further includes an effective amount of plasticizer, e.g. triethyl citrate. Preformulated aqueous dispersions of ethylcellulose, such as AQUACOAT™ or SURELEASE™ products, may be used. If a SURELEASE™ product is used, it is not necessary to separately add a plasticizer.

The hydrophobic material may be selected from the group consisting of alkylcellulose, acrylic and methacrylic acid polymers and copolymers, shellac, zein, fatty oils, hydrogenated castor oil, hydrogenated vegetable oil, or mixtures thereof. In certain preferred embodiments, the hydrophobic material can be a pharmaceutically acceptable acrylic polymer including, but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylicacid alkylamine copolymer, poly(methyl methacrylate), poly(methacrylic acid anhydride), polymethacrylate, polyacrylamide, poly (methacrylic acid anhydride), and glycidyl methacrylate copolymers. In alternate embodiments, the hydrophobic material can be selected from materials such as one or more hydroxyalkyl celluloses such as hydroxypropyl methylcellulose. The hydroxyalkyl cellulose can preferably be a hydroxy ($C_1$ to $C_6$) alkyl cellulose, such as hydroxypropylcellulose, hydroxypropylmethylcellulose, or preferably hydroxyethylcellulose. The amount of the hydroxyalkyl cellulose in the present oral dosage form can be determined, in part, by the precise rate of active agents (e.g., the components of the compositions of the invention) desired and may vary from about 1% to about 80%.

In embodiments of the present invention where the coating comprises an aqueous dispersion of a hydrophobic polymer, the inclusion of an effective amount of a plasticizer in the aqueous dispersion of hydrophobic polymer can further improve the physical properties of the film. For example, because ethylcellulose has a relatively high glass transition temperature and does not form flexible films under normal coating conditions, it may be necessary to plasticize the ethylcellulose before using it as a coating material. Generally, the amount of plasticizer included in a coating solution can be based on the concentration of the film-former, e.g., most often from about 1 percent to about 50 percent by weight of the film-former. Concentration of the plasticizer, however, can be preferably determined after careful experimentation with the particular coating solution and method of application.

Examples of suitable plasticizers for ethylcellulose include water-insoluble plasticizers such as dibutyl sebacate, diethyl phthalate, triethyl citrate, tributyl citrate, and triacetin, although other water-insoluble plasticizers (such as acetylated monoglycerides, phthalate esters, castor oil, etc.) may be used. Triethyl citrate may be an especially preferred plasticizer for the aqueous dispersions of ethyl cellulose of the present invention.

Examples of suitable plasticizers for the acrylic polymers of the present invention include, but are not limited to, citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as EUDRAGIT™ RL/RS lacquer solutions include polyethylene glycols, propylene glycol, diethyl phthalate, castor oil, and triacetin. Triethyl citrate may be an especially preferred plasticizer for aqueous dispersions of ethyl cellulose. It has further been found that addition of a small amount of talc may reduce the tendency of the aqueous dispersion to stick during processing and acts a polishing agent.

One commercially available aqueous dispersion of ethylcellulose is the AQUACOAT™ product which is prepared by dissolving the ethylcellulose in a water-immiscible organic solvent and then emulsifying the ethylcellulose in water in the presence of a surfactant and a stabilizer. After homogenization to generate submicron droplets, the organic solvent can be evaporated under vacuum to form a pseudolatex. The plasticizer will not be incorporated into the pseudolatex during the manufacturing phase. Thus, prior to using the pseudolatex as a coating, the AQUACOAT™ product can be mixed with a suitable plasticizer.

Another aqueous dispersion of ethylcellulose is commercially available as SURELEASE™ product (Colorcon, Inc., West Point, Pa., U.S.A.). This product can be prepared by incorporating plasticizer into the dispersion during the manufacturing process. A hot melt of a polymer, plasticizer (dibutyl sebacate), and stabilizer (oleic acid) can be prepared as a homogeneous mixture which can then be diluted with an alkaline solution to obtain an aqueous dispersion which can be applied directly onto substrates.

In one embodiment, the acrylic coating can be an acrylic resin lacquer used in the form of an aqueous dispersion, such as that which is commercially available from Rohm Pharma under the trade name EUDRAGIT™. In additional embodiments, the acrylic coating can comprise a mixture of two acrylic resin lacquers commercially available from Rohm Pharma under the trade names EUDRAGIT™ RL 30 D and EUDRAGIT™ RS 30 D. EUDRAGIT™ RL 30 D and EUDRAGIT™ RS 30 are copolymers of acrylic and methacrylic esters with a low content of quaternary ammonium groups, the molar ratio of ammonium groups to the remaining neutral (meth)acrylic esters being 1:20 in EUDRAGIT™ RL 30 and 1:40 in EUDRAGIT™ RS 30 D. The mean molecular weight is about 150,000 Daltons. The code designations RL (high permeability) and RS (low permeability) refer to the permeability properties of these agents. EUDRAGIT™ RL/RS mixtures are insoluble in water and in digestive fluids; however, coatings formed from them are swellable and permeable in aqueous solutions and digestive fluids.

The EUDRAGIT™ RL/RS dispersions may be mixed together in any desired ratio in order to ultimately obtain a controlled-release formulation having a desirable dissolution profile. Desirable controlled-release formulations may be obtained, for instance, from a retardant coating derived from one of a variety of coating combinations, such as 100% EUDRAGIT™ RL; 50% EUDRAGIT™ RL and 50% EUDRAGIT™ RS; or 10% EUDRAGIT™ RL and EUDRAGIT™ 90% RS. Of course, one skilled in the art will recognize that other acrylic polymers may also be used, for example, others under the EUDRAGIT™ brand. In addition to modifying the dissolution profile by altering the relative amounts of different acrylic resin lacquers, the dissolution profile of the ultimate product may also be modified, for example, by increasing or decreasing the thickness of the retardant coating.

The stabilized product may be obtained by subjecting the coated substrate to oven curing at a temperature above the Tg (glass transition temperature) of the plasticized acrylic polymer for the required time period, the optimum values for temperature and time for the particular formulation being determined experimentally. In certain embodiments of the present invention, the stabilized product is obtained via an oven curing conducted at a temperature of about 45° C. for a time period from about 1 to about 48 hours. It is also contemplated that certain products coated with the controlled-release coating of the present invention may require a curing time longer than 24 to 48 hours, e.g., from about 48 to about 60 hours or more.

The coating solutions preferably contain, in addition to the film-former, plasticizer, and solvent system (i.e., water), a colorant to provide elegance and product distinction. Color may be added to the solution of the compositions of the invention instead of, or in addition to the aqueous dispersion of hydrophobic material. For example, color may be added to an AQUACOAT™ product via the use of alcohol or propylene glycol based color dispersions, milled aluminum lakes and opacifiers such as titanium dioxide by adding color with shear to the water soluble polymer solution and then using low shear to the plasticized AQUACOAT™ product.

Alternatively, any suitable method of providing color to the formulations of the present invention may be used. Suitable ingredients for providing color to the formulation when an aqueous dispersion of an acrylic polymer is used include titanium dioxide and color pigments, such as iron oxide pigments. The incorporation of pigments, may, however, increase the retardant effect of the coating.

Spheroids or beads coated with the compositions of the invention can be prepared, for example, by dissolving the compositions of the invention in water and then spraying the solution onto a substrate, for example, non pareil 18/20 beads, using a Wuster insert. Optionally, additional ingredients can also be added prior to coating the beads in order to assist the binding of the compositions of the invention to the beads, and/or to color the solution, etc. For example, a product which includes hydroxypropyl methycellulose with or without colorant (e.g., OPADRY™ product, commercially available from Coloron, Inc.) may be added to the solution and the solution mixed (e.g., for about 1 hour) prior to application onto the beads. The resultant coated substrate, beads in this example, may then be optionally overcoated with a barrier agent to separate the compositions of the invention from the hydrophobic controlled release coating. An example of a suitable barrier agent is one which comprises hydroxypropyl cellulose. However, any film-former known in the art may be used. It is preferred that the barrier agent does not affect the dissolution rate of the final product.

Immediate release particles according to the present invention may be coated with a controlled release coating in order to change the release rate to obtain the dissolution rates according to the present invention.

Press Coated, Pulsatile Dosage Form

In another embodiment of the present invention, the compositions of the invention can be administered via a press coated pulsatile drug delivery system suitable for oral administration with a controlled release component, which contains a compressed blend of an active agent (e.g., the components of the compositions of the invention) and one or more polymers, substantially enveloped by an immediate release component, which contains a compressed blend of the active agent and hydrophilic and hydrophobic polymers. The immediate-release component preferably comprises a compressed blend of active agent and one or more polymers with disintegration characteristics such that the polymers disintegrate rapidly upon exposure to the aqueous medium.

The controlled-release component preferably can comprise a combination of hydrophilic and hydrophobic polymers. In this embodiment, once administered, the hydrophilic polymer will dissolve away to weaken the structure of the controlled-release component, and the hydrophobic polymer will retard the water penetration and help to maintain the shape of the drug delivery system.

In accordance with the present invention, the term "polymer" includes single or multiple polymeric substances, which can swell, gel, degrade or erode on contact with an aqueous environment (e.g., water). Examples include alginic acid, carboxymethylcellulose calcium, carboxymethylcellulose sodium, colloidal silicon dioxide, croscarmellose sodium, crospovidone, guar gum, magnesium aluminum silicate, methylcellulose, microcrystalline cellulose, polacrilin potassium, powdered cellulose, pregelatinized starch, sodium alginate, sodium starch glycolate, starch, ethylcellulose, gelatin, hydroxyethyl cellulose, hydroxypropyl cellulose, hydroxypropyl methylcellulose, polymethacrylates, povidone, pregelaiinized starch, shellac, and zein, and combinations thereof.

The term "hydrophilic polymers" as used herein includes one or more of carboxymethylcellulose, natural gums such as guar gum or gum acacia, gum tragacanth, or gum xanthan, hydroxyethyl cellulose, hydroxypropyl cellulose, hydroxypropyl methylcellulose, methylcellulose, and povidone, of which hydroxypropyl methylcellulose is further preferred.

The term "hydrophilic polymers" can also include sodium carboxymethycellulose, hydroxymethyl cellulose, polyethelene oxide, hydroxyethyl methyl cellulose, carboxypolymethylene, polyethelene glycol, alginic acid, gelatin, polyvinyl alcohol, polyvinylpyrrolidones, polyacrylamides, polymethacrylamides, polyphosphazines, polyoxazolidines, poly(hydroxyalkylcarboxylic acids), an alkali metal or alkaline earth metal, carageenate alginates, ammonium alginate, sodium alganate, or mixtures thereof.

The hydrophobic polymer of the drug delivery system can be any hydrophobic polymer which will achieve the goals of the present invention including, but not limited to, one or more polymers selected from carbomer, carnauba wax, ethylcellulose, glyceryl palmitostearate, hydrogenated castor oil, hydrogenated vegetable oil type 1, microcrystalline wax, polacrilin potassium, polymethacrylates, or stearic acid, of which hydrogenated vegetable oil type 1 is preferred. Hydrophobic polymers can include, for example, a pharmaceutically acceptable acrylic polymer, including, but not limited to, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methethyl methacrylate) copolymer, polyacrylamide, aminoalkyl methacrylate copolymer, poly(methacrylic acid anhydride), and glycidyl methacrylate copolymers. Additionally, the acrylic polymers may be cationic, anionic, or non-ionic polymers and may be acrylates, methacrylates, formed of methacrylic acid or methacrylic acid esters. The polymers may also be pH dependent.

The present invention also provides a method for preparing a press coated, pulsatile drug delivery system comprising the compositions of the invention suitable for oral administration. This method can include the steps of combining an effective amount of the components of the compositions of the invention, or a pharmaceutically acceptable salt thereof, and a polymer to form an immediate-release component; combining an effective amount of an active agent (e.g., the components of the compositions of the invention), or a pharmaceutically acceptable salt thereof, and a combination of hydrophilic and hydrophobic polymers to form a controlled release component; and press coating the controlled-release component to substantially envelop the immediate release component.

A preferred embodiment further can include the steps of combining an effective amount of an active agent (e.g., the components of the compositions of the invention), or a pharmaceutically acceptable salt thereof, and a polymer to form an immediate release component, and press coating the immediate release component to substantially envelop the controlled release component. In another preferred embodiment, the combining steps can be done by blending, wet granulation, fluid-bed granulation, or dry granulation according to methods recognized in the art.

The agents of the invention can also be mixed with other active materials which do not impair the desired action, or with materials that supplement the desired action, such as antacids, H2 blockers and anti-inflammatory agents. Higher concentrations, up to about 98% by weight of the components of the compositions of the invention may be included.

The dosage form of the invention may be administered to mammalian subjects, including: humans, monkeys, apes, dogs, cats, cows, horses, rabbits, pigs, mice and rats.

The dosage form of the invention may be administered orally (e.g., in liquid form within a solvent such as an aqueous or non-aqueous liquid, or within a solid carrier), rectally, parenterally, intracisternally, intravaginally, intraperitoneally, topically (as by powders, ointments, lotion, gels, drops, transdermal patch or transcutaneous patch), bucally, in bronchial form or as an oral or nasal spray. The term "parenteral" as used herein refers to modes of administration which include intravenous (e.g., within a dextrose or saline solution), intramuscular, intrasternal, subcutaneous, intracutaneous, intrasynovial, intrathecal, periostal, intracerebroventricularly, intra-articular injection and/or infusion. Alternative methods include administration by pump or continuous infusion, injection (e.g., as a suspension or as an emulsion in a pharmaceutically acceptable liquid or mixture of liquids), or liposomes. Administration can be performed daily, weekly, monthly, every other month, quarterly or any other schedule of administration as a single dose injection or infusion, multiple doses, or in continuous dose form. The administration of the pharmaceutical compositions of the present invention can be intermittent or at a gradual, continuous, constant or controlled rate to a subject. In addition, the time of day and the number of times per day that dosage form(s) is administered can vary.

For parenteral administration, in one embodiment, the agents of the invention can be formulated generally by mixing it at the desired degree of purity, in a unit dosage injectable form (solution, suspension, or emulsion), with a pharmaceutically acceptable carrier(s) described above.

Any dosage form used for therapeutic administration should be sterile. Sterility can readily be accomplished by filtration through sterile filtration membranes (e.g., 0.2 micron membranes). Therapeutics generally are placed into a container having a sterile access port, for example, an intravenous solution bag or vial having a stopper pierceable by a hypodermic injection needle.

The appropriate dose of the compound will be that amount effective to prevent occurrence of the symptoms of the food allergy, COPD or GERD and/or other gastrointestinal conditions ameliorated by proper histamine management or to treat some symptoms of the food allergy, COPD or GERD and/or other gastrointestinal conditions ameliorated by proper histamine management from which the patient suffers. By "effective amount", "therapeutic amount" or "effective dose" is meant that amount sufficient to elicit the desired pharmacological or therapeutic effects, thus resulting in effective prevention or treatment of the disorder or condition. Prevention of the food allergy, COPD, GERD and/or other gastrointestinal conditions ameliorated by proper histamine management can be manifested by delaying the onset of the symptoms of food allergy, COPD or GERD (e.g., acid reflux, heartburn, a burning sensation in the chest, occasionally a bitter taste in the mouth, cough, back pain) and/or other gastrointestinal conditions ameliorated by proper histamine management. Treatment of the disorder can be manifested by a decrease in the symptoms associated with food allergies, COPD, GERD and/or other gastrointestinal conditions ameliorated by proper histamine management or an amelioration of the recurrence of the symptoms of the food allergies, COPD, GERD and/or other gastrointestinal conditions ameliorated by proper histamine management.

Kits of the Invention

In a further embodiment, the present invention provides kits (i.e., a packaged combination of reagents with instructions) containing the agents of the invention useful for inhibiting, preventing or COPD, treating food allergies, GERD and/or other gastrointestinal conditions ameliorated by proper histamine management.

The kit can contain a pharmaceutical composition that includes one or more agents of the invention effective for inhibiting, preventing or treating COPD, food allergies, GERD and/or other gastrointestinal conditions, and an acceptable carrier or adjuvant, e.g., pharmaceutically acceptable buffer, such as phosphate-buffered saline, Ringer's solution or dextrose solution. It may further include other materials desirable from a commercial and user standpoint, including other buffers, diluents, filters, needles, syringes, and package inserts with instructions for use.

The agents may be provided as dry powders, usually lyophilized, including excipients that upon dissolving will provide a reagent solution having the appropriate concentration.

The kit comprises one or more containers with a label and/or instructions. The label can provide directions for carrying out the preparation of the agents for example, dissolving of the dry powders, and/or treatment for COPD, food allergy, GERD and/or other gastrointestinal conditions ameliorated by proper histamine management.

The label and/or the instructions can indicate directions for in vivo use of the pharmaceutical composition. The label and/or the instructions can indicate that the pharmaceutical composition is used alone, or in combination with another agent to treat COPD, food allergy, GERD and/or other gastrointestinal conditions ameliorated by proper histamine management.

The label can indicate appropriate dosages for the agents of the invention as described supra.

Suitable containers include, for example, bottles, vials, and test tubes. The containers can be formed from a variety of materials such as glass or plastic. The container can have a sterile access port (for example the container can be an intravenous solution bag or a vial having a stopper pierceable by a needle such as a hypodermic injection needle).

ADVANTAGES OF THE INVENTION

Tritoqualine alone is traditionally used for the treatment of allergy and primarily allergic rhinitis. Ranitidine (an anti-H2 drug) is used for the treatment of ulcers and stomach irritation due to acids as well as GERD with marginal results on the management of GERD. Similarly, Loratadine (an anti-H1 drug) is used with little or no results in the management of stomach acids or GERD. However, it was demonstrated in this invention that Loratadine and/or Ranitidine showed statistically significant effectiveness in the management of GERD when combined with Tritoqualine. When Tritoqualine and Ranitidine were combined, the drug combination was effective for the treatment of GERD in for example, patients that did not respond well to PPI treatment. When all three drugs (Tritoqualine, Ranitidine and Loratadine) were combined, the combination showed remarkable effectiveness for the treatment of GERD, much better than the standard therapy using PPI alone. The Tritoqualine-based combinations are also effective in groups of GERD-suffering patients who also suffer from allergies, food allergies, asthma and other pulmonary conditions, mastoytocis. Improvement in both the GERD and other allergy symptoms, pulmonary symptoms may also be possible.

The use of Tritoqualine in GERD, food allergy and, especially to COPD, is novel. The magnitude of the therapeutic response shown herein due to Tritoqualine drug combinations in GERD patients could not be predicted by a major decrease in stomach acid alone. In fact stomach acid is physiologically needed for the digestion of foods. Tritoqualine, synergistically with other histamine blockers may also be acting on the Lower esophageal sphincter (LES). Treating LES is the key to amelioration of GERD.

Leukotriene Receptor Antagonists have been traditionally used for the treatment of asthma. Typically LRA is used alone or in combination with steroid drugs. When HDC inhibitors such as Tritoqualine and LRA such as Montelukast were combined to treat food allergy, the therapeutic results were superior to any of the current therapies. When an HDC inhibitor such as Tritoqualine and LRA such as Montelukast are further combined with an Anti-H2 drug such as Ranitide and/or an Anti-H1 drug such as Loratadine (as a combination of three or four drugs) concomitantly, (for example, combination of Tritoqualine, Montelukast, Ranitidine and Loratadine), remarkable effectiveness for the treatment of food allergy were observed. For example, patients became able to ingest foods that prior to treatment, produced moderate to severe allergic symptoms from allergic rhinitis to severe anaphylaxis prior to the treatment.

In COPD, patients are usually treated by several combinations of drugs taken at different time intervals by the patient. The effect of Tritoqualine on top of the drug combinations taken by the patients was surprising and unexpected. The fact that Tritoqualine unpredictably improved the condition of COPD, suggests that Tritoqualine may act in mechanisms beyond HDC inhibition.

EXAMPLES

Example 1

The effectiveness of the combination of tritoqualine with an anti-H1 and combination of tritoqualine with an anti-H1 and an anti-H2 was demonstrated in human studies.
Patient Cohort Patients at baseline had at least a one year history of GERD for whom treatment with proton pump inhibitors (PPI) did not satisfactorily manage GERD symptoms. Baseline patients were diagnosed with GERD and Respiratory symptoms of allergy such as Allergic Rhinitis and Asthma.

Two groups of patients were treated in this study. The first group (Group A) was treated with an HDC inhibitor, Tritoqualine at 200 mg daily and an anti-H1 drug, Loratadine at 10 mg daily. The second group (Group B) was treated with a combination of a HDC inhibitor, Tritoqualine at 200 mg daily; an anti-H1 drug, Loratadine at 10 mg daily, and an anti-H2 drug, Ranitidine at 150 mg daily. The demographic characteristics of the patients are shown on Table 1.

Patients were recruited based upon the aforementioned criteria, and were examined by a physician at the initial visit (To) and following visit (T1) set after 6-8 weeks of treatment with the relevant drug combination.
Results Each patient was scored in both the initial visit (T0) and the visit 6-8 weeks later (T1) by the physician. Scoring of the symptoms is shown in Table 2. Both groups showed improvement using either combination of two drugs (Group A: HDC inhibitor and anti-H1 drug) or three drugs (Group B: HDC inhibitor and anti-H1 drug and anti-H2 drug). Overall, Group B showed superior score compared to Group A.

Based on the data presented above, patients diagnosed with GERD were inadequately treated with PPI and AntiH1 drug alone prior to the treatments described in this invention (patients were taking AntiH1 to control allergic symptoms and not to control GERD). The average score of 6.4 which represents GERD symptoms such as heartburn, regurgitation, and cough was indicative of the discomfort and inadequate treatment.

Removal of the PPI and introduction of the HDC inhibitor such as Tritoqualine with anti-H1 drugs in one group and Tritoqualine plus anti-H2 drug such as Ranitidine on the other group clearly improved the symptoms of GERD, by 82.9% (100*(6.4−3.5)/3.5) and 209.5% (100*(6.5−2.1)/2.1), respectively.

TABLE 1

Summary of the population demographics

| | Age | Average Age | Interval | Female | Male |
|---|---|---|---|---|---|
| Group A | 20-60 | 44 | 15 | 31 | 14 |
| Group B | 20-60 | 46 | 13 | 13 | 10 |
| Total # of patients | | | | 44 | 24 |

TABLE 2

Scoring guide for the magnitude of symptoms for GERD patients

| Symptoms/ Scores | No symptoms | Moderate Symptoms | Symptoms occurring each day | Symptoms occurring each day and night |
|---|---|---|---|---|
| Heartburn | 0 | 1 | 2 | 3 |
| Regurgitation | 0 | 1 | 2 | 3 |
| Cough | 0 | 1 | 2 | 3 |
| Global Score | 0 | 3 | 6 | 9 |

TABLE 3

Results of the study

| | Global Score To (initial visit) | Global Score T1 (visit after 6-8 weeks) | p-value |
|---|---|---|---|
| Group A | 6.4 | 3.5 | 0.005 |
| Group B | 6.5 | 2.1 | 0.002 |
| p-value | NS | 0.01 | |

NS = Not significant

Example 2

The effectiveness of the combination of tritoqualine with an anti-H1, combination of tritoqualine with an anti-H2 and combination of tritoqualine with both anti-H1 and anti-H2 was demonstrated in human studies.

Patient Cohort

Patients at baseline had at least one year history of GERD, for whom treatment with proton-pump inhibitors, anti-H1, anti-H2 and combination of anti-H1 and anti-H2 yielded unsatisfactory management of GERD symptoms. Baseline patients had received anti-H2 in the dosages range of 400-800 mg of Ranitidine per day, anti-H1 in the dosage range of about 10 mg Loratadine per day, and proton pump inhibitors (PPI) in the dosage range of about 40-60 mg of Omeprazole or Esomeprazole per day. The baseline patients were diagnosed with GERD and Respiratory symptoms of allergy such as Allergic Rhinitis and Asthma.

The one year history of allergies was confirmed with two positive prick tests. The list of prick test included *Dermatophagoid Pteronysinus, Dermatophagoid Farinae*, and cat and dog dander; food allergen such as wheat egg, soy, potato, peanut and tomato proteins; fungal proteins such as alternaria, mucor, and apergillus; pollen proteins such as birch tree, cypress tree, *Quercus* tree, *lolium perenne* and ray grass pollen Three groups of patients were treated in this study. The first group, Group A, was treated with an HDC inhibitor, Tritoqualine, 200 mg daily and an Anti-H1 drug, Loratadine, 10 mg daily. The second group, Group B, was treated with a combination of a HDC inhibitor Tritoqualine, 200 mg daily; an Anti-H1 drug, loratadine 10 mg daily, and an Anti-H2 drug, Ranitidine, 150 mg daily. The third group, Group C, was treated with an HDC inhibitor, Tritoqualine, 200 mg daily, and an Anti-H2 drug, Ranitidine, 150 mg daily.

The study population characteristics of the patients are shown on Table 4.

Patients were recruited based upon the aforementioned criteria, and were examined by an Allergist at the initial visit (To) and another doctor visitation (T1) set 6-8 weeks after treatment using the relevant drug combination (three drug combinations used described above).

Each patient was examined by the allergist both by a physical exam and answering a standard questionnaire. The questionnaire included questions such as whether the patient took proton-pump inhibitors and whether and the frequency at which the patient experienced heartburn, regurgitation and cough. Each patient was then assigned a score by the allergist for each of the GERD symptoms pursued in this study. Scores were assigned both during the initial visit (To) and the visit (T1) (scheduled within 6-8 weeks from T(o)). The severity of the following symptoms was assessed: heartburn, regurgitation, and cough. If the patient presented no symptoms of any of the specific attribute (heartburn, regurgitation, and cough) was assigned a 0 score for that attribute. Moderate symptoms (when the symptom occurs in the frequency of less than once per day) were given the score of 1. Symptoms occurring each day were given a score of 2 and symptoms occurring each day and night the score of 3. The scores of each symptom were added together to result in the global GERD score for each patient. Global scores were then compared from visits T (o) and T(1). Significant reduction in global scores indicated that the therapy improved the global GERD condition for each patient. A summary of the scoring system is shown on Table 5. The average T(o) and T1 scores for all male and female patients was calculated (need standard deviation) and reported in Table 6. Conducting a t-test, the p-value for each group was calculated. P-Values<0.05 would indicate that symptoms at visit T(o) and T(1) are significantly different from each other. If the total score at visit T(1) is significantly lower than at visit T(o) the it will be concluded that the effect of the drug combination was positive and therefore the treatment of the relevant combination of drugs, efficacious.

Results and Discussion

All groups, A, B and C, showed an improvement using all three combinations of drugs (Group A: HDC inhibitor and AntiH1 drug); (Group B: HDC inhibitor and AntiH1 drug and Anti H2 drug) and (Group C: HDC inhibitor and AntiH2 drug). Overall, groups B and C showed superior score compared to group A. It is therefore concluded that combinations of and HDC inhibitor such as Tritoqualine plus AntiH2 drugs such as Ranitidine at low dosages is an effective way to control the symptoms of GERD of allergic patients that are not responding to proton pump inhibitors or Anti H2 drugs alone. The treatment in group A is also effective in treating GERD. The results however of groups B and C are superior to group A.

TABLE 4

Summary of the patient details in the study

|  | Age | Average Age | Interval | Female | Male |
|---|---|---|---|---|---|
| Group A | 20-60 | 44 | 15 | 31 | 14 |
| Group B | 20-60 | 46 | 13 | 13 | 10 |
| Group C | 20-60 | 48 | 12 | 1 | 2 |
| Total |  |  |  | 45 | 26 |
| Percentage |  |  |  | 63 | 37 |

TABLE 5

Symptoms

| Scoring | No symptoms | Moderate Symptoms | Symptoms occurring each day | Symptoms occurring each day and night |
|---|---|---|---|---|
| Heartburn | 0 | 1 | 2 | 3 |
| Regurgitation | 0 | 1 | 2 | 3 |
| Cough | 0 | 1 | 2 | 3 |
| Global Score | 0 | 3 | 6 | 9 |

TABLE 6

|  | Global Score GERD T(o) (initial visit) | Global Score GERD T1 (visit after 6-8 weeks) | P value |
|---|---|---|---|
| Group A | 6.4 | 3.5 | 0.005 |
| Group B | 6.5 | 2.1 | 0.002 |
| Group C | 6.5 | 2.0 | 0.01 |
| P value | NS |  | 0.01 |

Example 3

Figure 2:
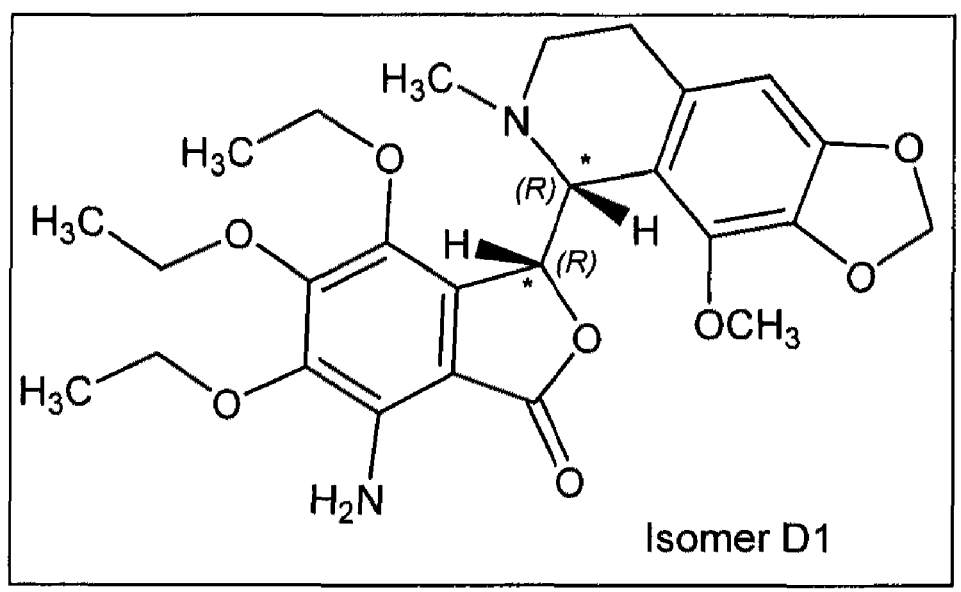
FIG. 2 illustrates the sterical structure of the tritoqualine diastereomer D1.
Figure 3:
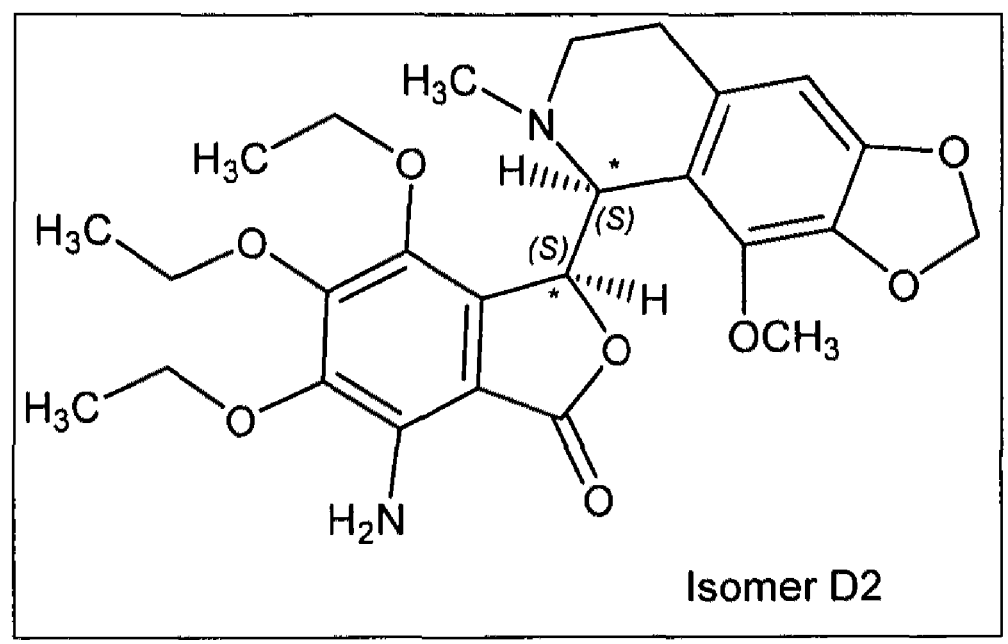
FIG. 3 illustrates the sterical structure of the tritoqualine diastereomer D2.

The known chemical structure of tritoqualine, illustrated in FIG. 1, is characterized by, amongst other structural features, the presence of two asymmetric carbons, A and B (marked with asterisk). Thus, depending on the method of synthesis, tritoqualine active pharmaceutical ingredient can be produced as either one or two diastereomeric structures each one comprising of its corresponding two mirror images, enantiomers. Thus, tritoqualine can exist as either two or four possible isomeric structures. Using the convention of R and S designation in each asymmetric carbon, one of the two possible diastereomeric structures will be comprised of the RR and SS enantiomers, and the other of RS and SR enantiomers. Embodiments of the two enantiomers include an isolated stereoisomer of tritoqualine having the structure D1 of FIG. 2 and an isolated stereoisomer of tritoqualine having the structure D2 of FIG. 3 and pharmaceutical compositions thereof.

Materials and Methods

Extraction of tritoqualine from tablets: Forty 100 mg tritoqualine tablets were crushed using mortar and pestle and the white powder was transferred to an Erlenmeyer flask. Addition of 400 mL ethyl acetate resulted in the formation of a fine white suspension. The suspension was allowed to stir for 1 hour under ambient conditions. Filtration of all insoluble matter, removal of solvent by rotary evaporation afforded a white crystalline solid. This solid was then dissolved in approximately 100 mL of dichloromethane. Hexane was added to the above solution until it became cloudy. After overnight storage at room temperature, Tritoqualine crystalline material formed at the bottom of the glass affording 3.5 g of pure tritoqualine.

Analytical Separation and Isolation of Tritoqualine Stereoisomers:

Thin layer chromatography: various proportions of ethyl acetate/hexane, dichloromethane/hexane, and ethyl acetate dichloromethane were used in conjunction with silica-based thin layer chromatography to identify the number of compounds available in the mixture. In all cases of mobile phase mixtures, there was only one single spot observed (seen under UV light) indicating the presence of only one diastereomer. The two enantiomers comprising the diastereomer could not be resolved using silica-based thin layer chromatography.

HPLC separation of tritoqualine enantiomers: HPLC separation was conducted using an Agilent 1100 HPLC system equipped with a quaternary pump, injector, diode array detector and a Jasco OR-990 polarimetric detector. The successful chromatographic separation utilized the chiral HPLC column CHIRALPAK®IA (250 mm, 4.6 mm, 5 μm) with the following conditions: mobile phase: n-heptane/dichloromethane 60:40; flow rate 1 ml/min; temp 25° C.; tritoqualine concentration injected was 8 g/l in mobile phase; injection volume 1 μl; UV detection: 290 nm. UV spectra for each enantiomer were obtained using the diode array detector and absorption of polarized light using a polarimetric detector.

HPLC purification of tritoqualine enantiomers: Purification of each tritoqualine enantiomer was conducted using a similar Agilent HPLC with a preparatory chiral column CHIRALPAK®IA (250 mm, 4.6 mm, 5 μm). Mobile phase: n-heptane dichloromethane 60:40; flow rate 20 mL/min; temp 25° C., UV detection 250 mm. Each enantiomer was collected as was eluted from the column. To ensure purity of each enantiomer HPLC analysis using the analytical column CHIRALPAK®IA (250 mm, 4.6 mm, 5 μm), mobile phase: n-heptane/dichloromethane 60:40; flow rate 1 ml/min; temp 25° C.; UV detection: 250 nm. Enantiomer A eluted at retention time of −5.95 min and enantiomer B at retention time of 7.19 mins. Chemical purities for each isolated compound exceeded the 99.5%. Enantiomeric excess for enantiomer A was 99.5% and enantiomer B was 99.0%. Solvent removal afforded each isolated isomer as an amorphous white powder.

Characterization of the Commercial Mixture of Tritoqualine and of Each Isolated Enantiomer by NMR.

$^1$H NMR spectra were recorded on a Brucker AMX 500 (500 MHz). Chemical shifts are expressed in parts per million (δ) relative to residual solvents as internal standards.

$^1$H NMR characterization of the commercial tritoqualine product isolated from tablets: $^1$H NMR (CDCl$_3$) δ 6.36 (1H, s), 5.88 (2H, m), 5.59 (1H, d, J=1.71 Hz), 5.03 (2H, s), 4.54 (1H, s), 4.08 (9H, m), [3.08 (1H, m), 2.76 (1H, m), 2.56 (1H, m), 2.43 (1H, m)], 2.14 (3H, s), 1.39-1.45 (9H, m).

$^1$H NMR characterization of isolated enantiomer A: $^1$H NMR (CDCl$_3$) δ Ar 6.35 (1H, s,), O—, 5.87 (2H, m), 5.58 (1H, s), 5.02 (2H, s), 4.54 (1H, s), 4.08 (9H, m), [3.04 (1H, m), 2.79 (1H, m), 2.55 (1H, m), 2.41 (1H, m)], 2.13 (3H, s), 1.37-1.45 (9H, m).

$^1$H NMR characterization of isolated enantiomer B: $^1$H NMR (CDCl$_3$) δ 6.36 (1H, s,), 5.88 (2H, m), 5.58 (1H, d, J=1.71 Hz), 5.02 (2H, s), 4.54 (1H, s), OCH$_3$ 4.07 (9H, m), 3.04 (1H, m), 2.77 (1H, m), 2.55 (1H, m), 2.41 (1H, m), 2.13 (3H, s), 1.37-1.45 (9H, m).

Crystallography

Figure 6:
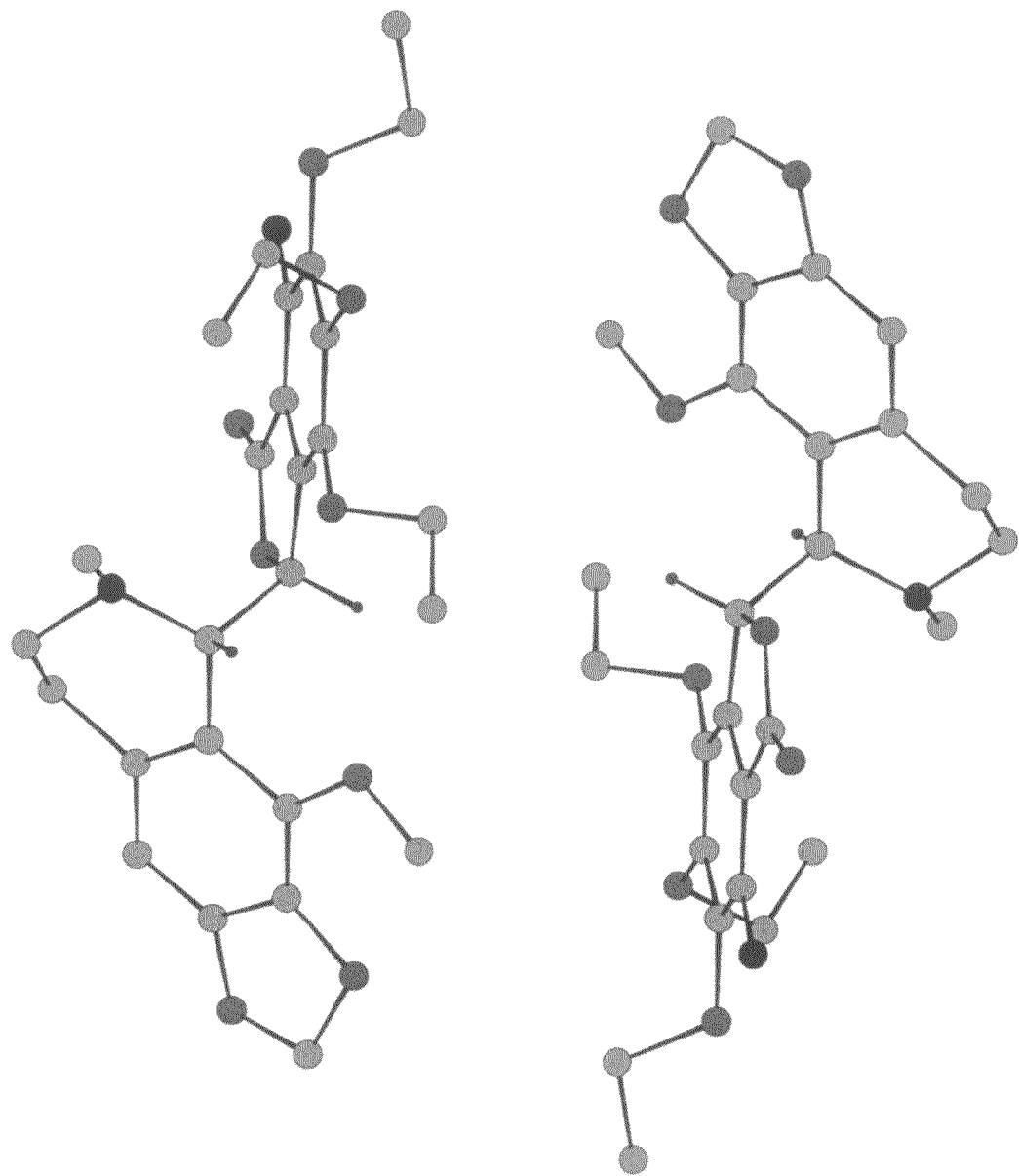
FIG. 6 illustrates the 3D-structures of the two stereoisomers (enantiomers) of FIGS. 4 and 5 as determined by X-Ray crystallography.

A crystal of tritoqualine, afforded by the recrystallization procedure described above, was chosen for X-Ray crystallography. The crystal structure of commercial tritoqualine was determined by an expert crystallographer. The data is reported in Tables S1-S5 and a picture of the existing structures is illustrated in FIG. 6 below.

Crystal Structure Determination $C_{26}H_{32}N_2O_8$

The Bruker X8-APEX X-ray diffraction instrument with Mo-radiation was used for data collection. All data frames were collected at low temperatures (T=90 K), using an ω, φ-scan mode (0.3° ω-scan width, hemisphere of reflections), and integrated using a Bruker SAINTPLUS software package. The intensity data were corrected for Lorentzian polarization. Absorption corrections were performed using the SADABS program. The SIR97 was used for direct methods of phase determination, and Bruker SHELXTL software for structure refinement and difference Fourier maps. Atomic coordinates, isotropic and anisotropic displacement parameters, of all the non-hydrogen atoms were refined, by means of a full matrix least-squares procedure on $F^2$. All H-atoms were included in the refinement, in calculated positions riding on the C atoms, with U[iso] fixed at 20% higher, than isotropic parameters of carbons atoms which they were attached. Drawing of molecule was performed using Ortep 3.

Crystal and structure parameters: size 0.38×0.20×0.10 mm$^3$, monoclinic, space group P2(1)/n, a=16.7348(6) Å, b=7.8819(3) Å, c=18.5117(6) Å, α=90.0° β=985090(10)° γ=90.0°, V=2414.85(15) Å$^3$, $\rho_{calcd}$=1.377 g/cm$^3$, $2\theta_{max}$=65.26°, Mo-radiation (λ=0.71073 Å), low temperature=90(2) K, reflections collected=33322, independent reflections=8434 ($R_{int}$=0.0372, $R_{sig}$=0.0382), 6524 (77.4%) reflections were greater than 2σ(I), index ranges 25<=h<=24, −11<=k<=10, −27<=l<=25, absorption coefficient μ=0.102 mm$^{-1}$ max/min transmission=0.9898 and 0.9621, 399 parameters were refined and converged at R1=0.0493, wR2=0.1210, with intensity I>2σ(I), the final difference map was 0.431 and −0.272 e.Å$^{-3}$.

Mass Spectrometry

Mass spectrometry results showed molecular ion peaks for each enantiomer to be 500. The mass spectrometry data was recorded on Applied Biosystems PI 100 electrospray mass spectrometer. The samples were run in positive mode and (M$^+$+1) values are reported 501.6 for enantiomer A and 501.5 for enantiomer B.

Results and Discussion

Separation, Characterization and Isolation of Tritoqualine Enantiomers:

Silica-based thin layer chromatography, was not able to separate and resolve any tritoqualine diastereomers. In general diastereomeric compounds can be separated in silica-based thin layer chromatography. Enantiomers, on the other hand cannot be separated by silica-based chromatography. A chiral solid phase is necessary to separate and resolve enantiomers. Therefore, it was postulated that the commercial tritoqualine material was, probably, a mixture of enantiomers.

Figure 4:
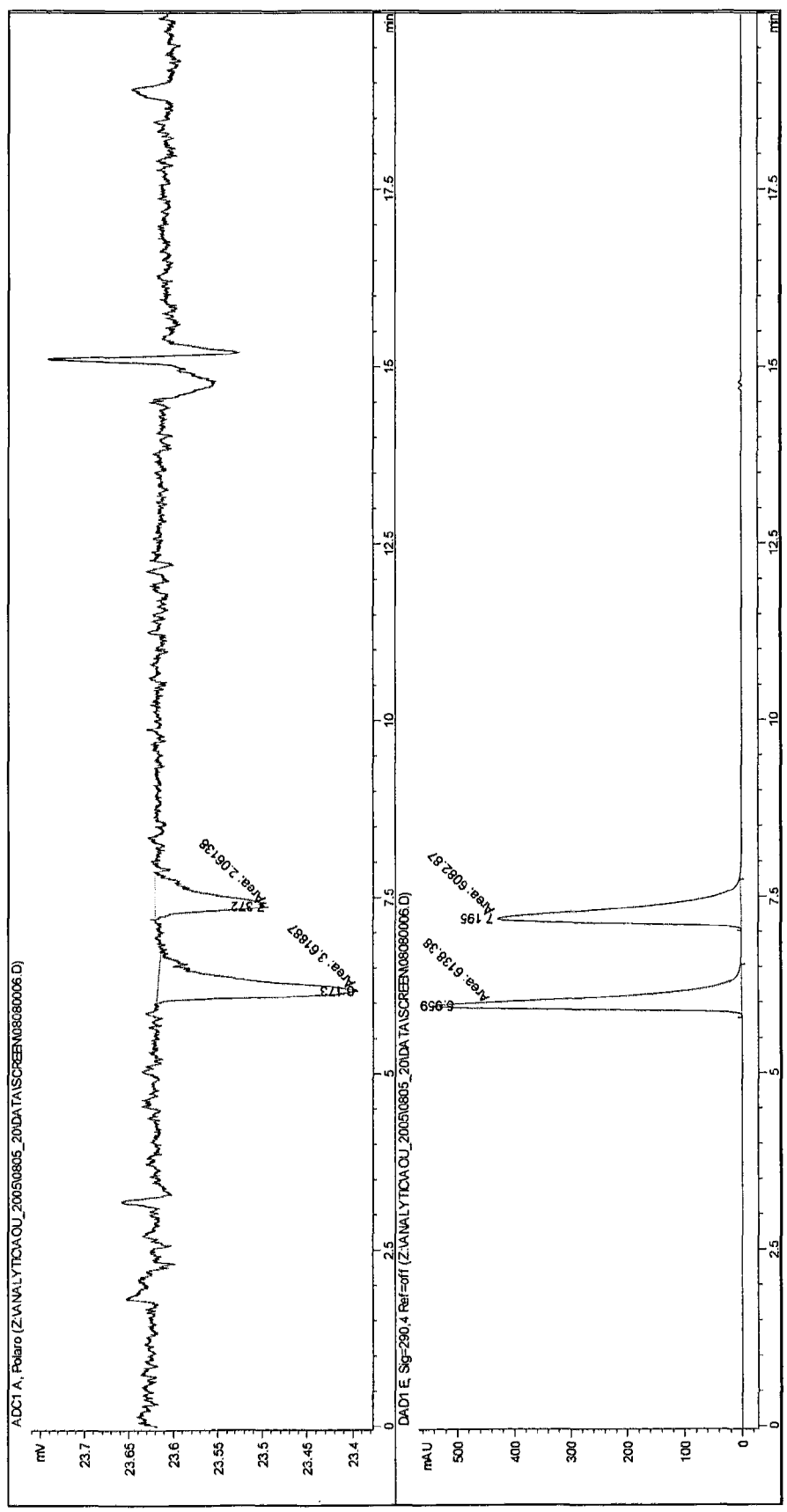
FIG. 4 shows a chromatogram of the separation of tritoqualine stereoisomers via a chiral column. In the bottom part, the UV absorbance at 190 nm has been detected, while the top part depicts polarimetric detection at an averaged absorption in the range of 200-800 nm.
Figure 5:
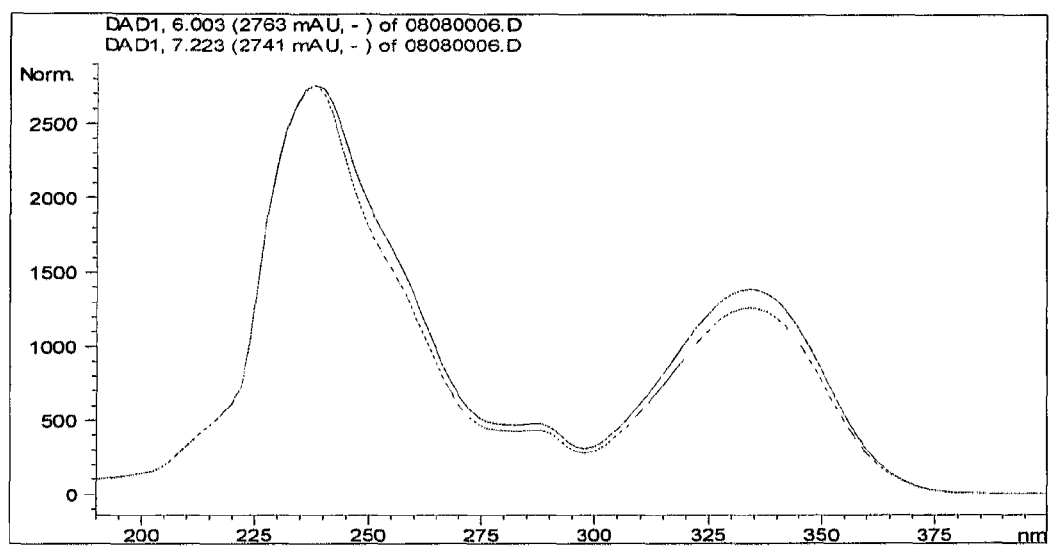
FIG. 5 shows a UV spectrum of each of the peaks of FIG. 4.

Chiral chromatography was employed in order to test commercial tritoqualine (two chiral centers) for the presence of enantiomers. FIG. 4 (bottom part) illustrates a representative chromatogram of tritoqualine chromatographed on a chiral column. Clearly, two distinct and well resolved peaks of approximately the same area could be identified, at 5.95 and 7.19 minutes respectively. Polarimetric detection (FIG. 4, top part) indicates that each peak on the chromatogram absorbs polarized light suggesting that each molecule eluting from the chiral column is an optically active compound. However, the polarimetric detector, in contrast to the standard polarimeters, does not measure the sign of the rotatory power at a given wavelength, but only gives an average response over a range of wavelengths (200-800 nm). As the sign of the rotatory power may change depending on the wavelength for the same isomer (for certain compounds), especially for compounds having UV absorption at high wavelengths (>300 nm) which is the case of tritoqualine (FIG. 5), it was not possible to draw conclusions by this technique beyond the notion that each peak represents an optical isomer. From the diode array detector available on the HPLC setup the UV spectrum of each peak was obtained as shown on FIG. 5. Both compounds show almost identical UV spectra, which is the case of enantiomers. To further confirm the presence of enantiomers, $^1$HNMR spectra of the mixture and of the individual components are identical. If two optically active diastereomers were present in the mixture, then two sets of peaks for each diastereomer would have been expected.

Diastereomer Identification in Commercial Tritoqualine:

The tritoqualine structure contains two chiral centers (FIG. 1). Thus, there could only be two possible diastereomeric structures. One comprised of the enantiomers RR and SS and a second comprised of the enantiomers RS and SR.

Based on the data generated above, the only reasonable conclusion was that commercial tritoqualine is a single diastereomeric structure. The challenge to find whether commercial tritoqualine is the RR/SS or the RS/SR remains.

To solve this issue, a single crystal from the recrystallized tritoqualine was identified and the crystal structure was determined by an expert crystallographer. The crystallography data, indicates that on the single tritoqualine crystal there are two molecules present that are enantiomers of a single diastereomer. The two enantiomers bear the RR and the SS configuration.

All relevant information is shown on Tables S1-S5 and the molecular structures of the two enantiomers are illustrated on FIG. 6.

Isolation of Tritoqualine Enantiomers for the Purposes of Biological Activity Determination:

Using the preparatory chiral column CHIRALPAK®IA (250 mm, 4.6 mm, 5 μm) and the HPLC system described above, the two enantiomers, enantiomer A and B have been successfully isolated as amorphous white powders.

Purification of Human Histidine Decarboxylase

The DNA encoding for residues 1-512 of human HDC was subcloned in the pGEX-6P-1 vector (GE-Healthcare). The recombinant plasmid transformed into the *Escherichia coli* BL21(DE3)pLysS strain. Transformed cultures were induced to express the HDC 1/512, which was purified by affinity chromatography using Glutathione sepharose (GE-Healthcare). 1/512 HDC was released from the fusion protein bound to the affinity chromatography support by digestion with the Pre-Scission™ protease (GE-Healthcare). The final preparations were dissolved in 50 mM potassium phosphate, 0.1 mM PLP, pH 7.0. Purity of the HDC 1/512 construct was checked by Coomassie blue staining and Western blotting, and was higher than 95% in the final preparations.

Human-HDC Activity Determination

HDC activity was assayed, as described in Engel at al. (1996) Biochem J. 320: 365-368, by measuring the production of $^{14}CO_2$ from L-[U-$^{14}$C]histidine (GE-Healthcare) in a mixture containing 0.2 mM dithiothreitol, 10 μM PLP, 10 mg/ml poly(ethylene glycol)-300, 100 mM potassium phosphate, pH 6.8, and purified protein in a total volume of 100 μL. When recombinant HDC was used, the concentration of L-[U-$^{14}$C]histidine was 13.3 mM (with 1/3 isotopic dilution). The released $^{14}$CO2 was measured as previously described for HDC activity determinations (Urdiales et al. (1992) FEBS Lett. 305, 260-264).

Assessment of Inhibitory Activity of Each Isomeric Component, Versus the Mixture:

10 μM concentration of each isomer, A and B (A corresponds to the isolated pure isomer eluting at 5.9 minutes, B corresponds to the isolated pure isomer eluting at 7.1 minutes of the chromatogram shown in FIG. 4 (bottom)) and their corresponding racemic mixture (starting material prior to separating the individual isomers, indicated as A+B) along with 4 μg of recombinant human HDC were used to assess the inhibitory effect of each isomer and the mixture on the enzymatic conversion of histidine to histamine. Table 7 summarizes results obtained. Results are presented as means of duplicates samples. As shown in Table 7, the pure isomers (isomer A and isomer B) have more activity compared to the racemic mix (A+B).

TABLE 7

Effect of compound A, B and A + B on activity of recombinant HDC at micromolar concentration.

| Sample | DPM | Activity (μmole/h) | Specific activity (μmole/h · mg prot) | % of control | % of inhibition |
|---|---|---|---|---|---|
| Control | 12340 | 0.35 | 87.00 | 100.00 | |
| Isomer A (10 μM final) | 8895 | 0.25 | 62.71 | 72.08 | 27.92 |
| Isomer B (10 μM final) | 7831 | 0.22 | 55.21 | 63.46 | 36.54 |
| Racemic mix A + B (10 μM final) | 10176 | 0.29 | 71.74 | 82.46 | 17.54 |

TABLE S1

Crystal data and structure refinement.

| | |
|---|---|
| Empirical formula | $C_{26}H_{32}N_2O_8$ |
| Formula weight | 500.54 |
| Temperature | 90(2) K |
| Wavelength | 0.71073 Å |
| Crystal system | Monoclinic |
| Space group | P2(1)/n |
| Unit cell dimensions | a = 16.7348(6) Å  □ = 90° |
| | b = 7.8819(3) Å  □ = 98.5090(10)° |
| | c = 18.5117(6) Å  □ = 90° |
| Volume | 2414.85(15) Å$^3$ |
| Z | 4 |
| Density (calculated) | 1.377 Mg/m$^3$ |
| Absorption coefficient | 0.102 mm$^{-1}$ |
| F(000) | 1064 |
| Crystal size | 0.38 × 0.20 × 0.10 mm$^3$ |
| Theta range for data collection | 2.22 to 32.63° |
| Index ranges | −25 <= h <= 24, −11 <= k <= 10, −27 <= l <= 25 |
| Reflections collected | 33322 |
| Independent reflections | 8434 [R(int) = 0.0372] |
| Completeness to theta = 32.63° | 95.7% |
| Absorption correction | Sadabs |
| Max. and min. transmission | 0.9898 and 0.9621 |
| Refinement method | Full-matrix least-squares on F$^2$ |
| Data/restraints/parameters | 8434/0/399 |
| Goodness-of-fit on F$^2$ | 1.021 |
| Final R indices [I > 2sigma(I)] | R1 = 0.0493, wR2 = 0.1210 |
| R indices (all data) | R1 = 0.0677, wR2 = 0.1309 |
| Largest diff. peak and hole | 0.431 and −0.272 e · Å$^{-3}$ |

TABLE S2

Atomic coordinates (×10$^4$) and equivalent isotropic displacement parameters (Å$^2$ × 10$^3$) U(eq) is defined as one third of the trace of the orthogonalized U$^{ij}$ tensor.

| | x | y | z | U(eq) |
|---|---|---|---|---|
| N(1) | 4187(1) | 505(1) | 7064(1) | 15(1) |
| N(2) | 2469(1) | 6526(1) | 7408(1) | 22(1) |
| O(1) | 4787(1) | 3926(1) | 7526(1) | 17(1) |
| O(2) | 8074(1) | 270(1) | 7914(1) | 30(1) |
| O(3) | 7817(1) | 1237(1) | 6723(1) | 25(1) |
| O(4) | 4067(1) | 5361(1) | 8264(1) | 22(1) |
| O(5) | 6084(1) | 1991(1) | 5982(1) | 19(1) |
| O(6) | 3737(1) | 2797(1) | 5250(1) | 20(1) |
| C(1) | 4114(1) | 4785(1) | 7666(1) | 16(1) |
| C(2) | 3536(1) | 4844(1) | 6994(1) | 16(1) |
| C(3) | 2767(1) | 5590(1) | 6881(1) | 17(1) |
| C(4) | 2330(1) | 5387(2) | 6178(1) | 20(1) |
| C(5) | 2649(1) | 4475(2) | 5638(1) | 20(1) |
| C(6) | 3433(1) | 3771(2) | 5762(1) | 18(1) |
| C(7) | 3863(1) | 3974(1) | 6453(1) | 15(1) |
| C(8) | 4689(1) | 3349(1) | 6771(1) | 15(1) |
| C(9) | 4825(1) | 1417(1) | 6743(1) | 14(1) |
| C(10) | 5687(1) | 1028(1) | 7087(1) | 15(1) |
| C(11) | 6312(1) | 1350(1) | 6668(1) | 16(1) |
| C(12) | 7096(1) | 1016(2) | 6998(1) | 19(1) |
| C(13A) | 8410(5) | 438(8) | 7244(5) | 32(1) |
| C(13B) | 8434(13) | 880(20) | 7355(13) | 43(4) |
| C(14) | 7249(1) | 432(2) | 7708(1) | 22(1) |
| C(15) | 6658(1) | 112(2) | 8126(1) | 23(1) |
| C(16) | 5857(1) | 420(2) | 7800(1) | 18(1) |
| C(17) | 5150(1) | 4(2) | 8183(1) | 22(1) |
| C(18) | 4479(1) | −737(2) | 7633(1) | 20(1) |
| C(19) | 6648(1) | 1882(2) | 5474(1) | 24(1) |
| C(20A) | 3999(3) | 3784(5) | 4676(2) | 27(1) |
| C(20B) | 3831(7) | 3420(13) | 4531(6) | 34(2) |
| C(21) | 4431(1) | 2557(2) | 4224(1) | 28(1) |
| O(7A) | 2204(2) | 4414(3) | 4960(2) | 18(1) |
| C(22A) | 1509(1) | 3252(2) | 4911(1) | 18(1) |
| C(23A) | 1771(2) | 1542(3) | 4685(2) | 44(1) |
| O(7B) | 2188(7) | 3888(8) | 4956(7) | 28(2) |
| C(22B) | 1726(6) | 2260(20) | 5010(5) | 93(5) |
| C(23B) | 1508(4) | 1574(8) | 4304(4) | 36(1) |
| O(8A) | 1549(3) | 6094(11) | 6050(4) | 20(1) |
| C(24A) | 1469(6) | 7557(10) | 5574(5) | 22(1) |
| O(8B) | 1575(10) | 5820(30) | 6002(10) | 28(4) |
| C(24B) | 1476(16) | 7230(30) | 5472(14) | 28(3) |
| C(25) | 578(1) | 7703(2) | 5283(1) | 29(1) |
| C(26) | 3628(1) | −354(2) | 6496(1) | 20(1) |

TABLE S3

Bond lengths [Å] and angles [°].

| | | | |
|---|---|---|---|
| N(1)—C(26) | 1.4661(14) | N(1)—C(18) | 1.4673(15) |
| N(1)—C(9) | 1.4828(14) | N(2)—C(3) | 1.3728(16) |
| N(2)—HN1 | 0.885(18) | N(2)—HN2 | 0.96(2) |
| O(1)—C(1) | 1.3714(13) | O(1)—C(8) | 1.4559(14) |
| O(2)—C(13B) | 1.36(2) | O(2)—C(14) | 1.3841(13) |
| O(2)—C(13A) | 1.442(10) | O(3)—C(12) | 1.3866(14) |
| O(3)—C(13A) | 1.424(9) | O(3)—C(13B) | 1.47(2) |
| O(4)—C(1) | 1.2090(15) | O(5)—C(11) | 1.3678(14) |
| O(5)—C(19) | 1.4294(14) | O(6)—C(6) | 1.3759(14) |
| O(6)—C(20A) | 1.436(5) | O(6)—C(20B) | 1.448(12) |
| C(1)—C(2) | 1.4590(15) | C(2)—C(7) | 1.3898(16) |

TABLE S3-continued

Bond lengths [Å] and angles [°].

| | | | |
|---|---|---|---|
| C(2)—C(3) | 1.4035(14) | C(3)—C(4) | 1.4036(17) |
| C(4)—O(8B) | 1.305(17) | C(4)—C(5) | 1.4000(18) |
| C(4)—O(8A) | 1.409(6) | C(5)—O(7A) | 1.361(4) |
| C(5)—C(6) | 1.4115(15) | C(5)—O(7B) | 1.454(11) |
| C(6)—C(7) | 1.3801(16) | C(7)—C(8) | 1.5043(14) |
| C(8)—C(9) | 1.5419(15) | C(9)—C(10) | 1.5197(14) |
| C(10)—C(16) | 1.3930(16) | C(10)—C(11) | 1.4144(15) |
| C(11)—C(12) | 1.3880(14) | C(12)—C(14) | 1.3810(18) |
| C(14)—C(15) | 1.3662(19) | C(15)—C(16) | 1.4065(15) |
| C(15)—H(15) | 0.9500 | C(16)—C(17) | 1.5032(17) |
| C(17)—C(18) | 1.5168(17) | C(20A)—C(21) | 1.529(5) |
| C(20B)—C(21) | 1.402(13) | O(7A)—C(22A) | 1.473(4) |
| C(22A)—C(23A) | 1.496(3) | O(7B)—C(22B) | 1.509(17) |
| C(22B)—C(23B) | 1.412(10) | O(8A)—C(24A) | 1.445(12) |
| C(24A)—C(25) | 1.512(10) | O(8B)—C(24B) | 1.47(3) |
| C(24B)—C(25) | 1.54(3) | | |
| C(26)—N(1)—C(18) | 108.46(9) | C(26)—N(1)—C(9) | 110.92(9) |
| C(18)—N(1)—C(9) | 115.39(8) | C(3)—N(2)—HN1 | 115.2(12) |
| C(3)—N(2)—HN2 | 114.0(11) | HN1—N(2)—HN2 | 116.8(16) |
| C(1)—O(1)—C(8) | 110.92(8) | C(13B)—O(2)—C(14) | 107.1(9) |
| C(14)—O(2)—C(13A) | 104.7(3) | C(12)—O(3)—C(13A) | 104.7(4) |
| C(12)—O(3)—C(13B) | 103.4(9) | C(11)—O(5)—C(19) | 117.87(9) |
| C(6)—O(6)—C(20A) | 113.09(18) | C(6)—O(6)—C(20B) | 123.1(5) |
| O(4)—C(1)—O(1) | 121.60(10) | O(4)—C(1)—C(2) | 130.14(10) |
| O(1)—C(1)—C(2) | 108.26(10) | C(7)—C(2)—C(3) | 123.33(10) |
| C(7)—C(2)—C(1) | 108.53(9) | C(3)—C(2)—C(1) | 128.12(11) |
| N(2)—C(3)—C(2) | 122.73(11) | N(2)—C(3)—C(4) | 121.72(10) |
| C(2)—C(3)—C(4) | 115.48(11) | O(8B)—C(4)—C(5) | 114.4(10) |
| O(8B)—C(4)—C(3) | 123.7(9) | C(5)—C(4)—C(3) | 121.34(10) |
| C(5)—C(4)—O(8A) | 121.6(3) | C(3)—C(4)—O(8A) | 117.0(3) |
| O(7A)—C(5)—C(4) | 117.59(17) | O(7A)—C(5)—C(6) | 120.30(18) |
| C(4)—C(5)—C(6) | 121.85(11) | C(4)—C(5)—O(7B) | 125.1(5) |
| C(6)—C(5)—O(7B) | 112.2(4) | O(6)—C(6)—C(7) | 120.53(9) |
| O(6)—C(6)—C(5) | 122.43(10) | C(7)—C(6)—C(5) | 116.79(11) |
| C(6)—C(7)—C(2) | 121.17(9) | C(6)—C(7)—C(8) | 130.40(10) |
| C(2)—C(7)—C(8) | 108.42(9) | O(1)—C(8)—C(7) | 103.86(8) |
| O(1)—C(8)—C(9) | 110.19(9) | C(7)—C(8)—C(9) | 116.21(9) |
| N(1)—C(9)—C(10) | 115.37(9) | N(1)—C(9)—C(8) | 110.29(8) |
| C(10)—C(9)—C(8) | 108.67(8) | C(16)—C(10)—C(11) | 121.12(9) |
| C(16)—C(10)—C(9) | 121.03(10) | C(11)—C(10)—C(9) | 117.83(9) |
| O(5)—C(11)—C(12) | 126.46(10) | O(5)—C(11)—C(10) | 116.61(9) |
| C(12)—C(11)—C(10) | 116.92(10) | C(14)—C(12)—O(3) | 110.05(9) |
| C(14)—C(12)—C(11) | 120.74(11) | O(3)—C(12)—C(11) | 129.17(11) |
| O(3)—C(13A)—O(2) | 107.6(5) | O(2)—C(13B)—O(3) | 109.6(14) |
| C(15)—C(14)—C(12) | 123.63(10) | C(15)—C(14)—O(2) | 127.12(12) |
| C(12)—C(14)—O(2) | 109.24(11) | C(14)—C(15)—C(16) | 116.61(11) |
| C(10)—C(16)—C(15) | 120.97(11) | C(10)—C(16)—C(17) | 117.20(9) |
| C(15)—C(16)—C(17) | 121.72(11) | C(16)—C(17)—C(18) | 108.89(10) |
| N(1)—C(18)—C(17) | 111.09(10) | O(6)—C(20A)—C(21) | 106.4(3) |
| C(21)—C(20B)—O(6) | 113.0(7) | C(5)—O(7A)—C(22A) | 113.4(3) |
| O(7A)—C(22A)—C(23A) | 108.44(19) | C(5)—O(7B)—C(22B) | 115.0(8) |
| C(23B)—C(22B)—O(7B) | 109.2(9) | C(4)—O(8A)—C(24A) | 114.7(6) |
| O(8A)—C(24A)—C(25) | 106.0(6) | C(4)—O(8B)—C(24B) | 112.0(16) |
| O(8B)—C(24B)—C(25) | 110.1(18) | | |

TABLE S4

Anisotropic displacement parameters (Å$^2$ × 10$^3$).
The anisotropic displacement factor exponent takes the form:
$-2\pi^2[h^2 a^{*2} U^{11} + \ldots + 2 hk\, a^* b^* U^{12}]$

| | U$^{11}$ | U$^{22}$ | U$^{33}$ | U$^{23}$ | U$^{13}$ | U$^{12}$ |
|---|---|---|---|---|---|---|
| N(1) | 15(1) | 14(1) | 16(1) | 1(1) | 4(1) | −2(1) |
| N(2) | 19(1) | 20(1) | 29(1) | 1(1) | 10(1) | 3(1) |
| O(1) | 16(1) | 16(1) | 19(1) | −2(1) | 1(1) | 1(1) |
| O(2) | 17(1) | 36(1) | 35(1) | −1(1) | −6(1) | 8(1) |
| O(3) | 12(1) | 27(1) | 36(1) | 3(1) | 2(1) | 2(1) |
| O(4) | 26(1) | 20(1) | 21(1) | −3(1) | 5(1) | 0(1) |
| O(5) | 15(1) | 23(1) | 19(1) | 5(1) | 5(1) | 3(1) |
| O(6) | 22(1) | 22(1) | 17(1) | 1(1) | 5(1) | 2(1) |
| C(1) | 17(1) | 13(1) | 21(1) | 0(1) | 4(1) | −1(1) |
| C(2) | 14(1) | 14(1) | 20(1) | 2(1) | 3(1) | 0(1) |
| C(3) | 15(1) | 15(1) | 23(1) | 4(1) | 7(1) | 1(1) |
| C(4) | 13(1) | 23(1) | 24(1) | 8(1) | 5(1) | 3(1) |
| C(5) | 14(1) | 27(1) | 19(1) | 6(1) | 2(1) | 1(1) |
| C(6) | 15(1) | 20(1) | 18(1) | 2(1) | 3(1) | 1(1) |
| C(7) | 13(1) | 14(1) | 18(1) | 3(1) | 3(1) | 1(1) |
| C(8) | 13(1) | 14(1) | 17(1) | 1(1) | 2(1) | 0(1) |
| C(9) | 13(1) | 14(1) | 15(1) | 1(1) | 2(1) | 0(1) |
| C(10) | 14(1) | 13(1) | 17(1) | −1(1) | 1(1) | 2(1) |
| C(11) | 15(1) | 14(1) | 19(1) | 0(1) | 1(1) | 2(1) |
| C(12) | 14(1) | 16(1) | 27(1) | 0(1) | 2(1) | 2(1) |
| C(13A) | 14(1) | 36(2) | 45(2) | 5(2) | −3(1) | 5(1) |
| C(13B) | 16(3) | 64(10) | 45(8) | 23(7) | −3(4) | −2(7) |
| C(14) | 17(1) | 19(1) | 28(1) | −3(1) | −5(1) | 5(1) |
| C(15) | 24(1) | 23(1) | 19(1) | 1(1) | −3(1) | 6(1) |

TABLE S4-continued

Anisotropic displacement parameters ($Å^2 \times 10^3$).
The anisotropic displacement factor exponent takes the form:
$-2\pi^2[h^2 a^{*2} U^{11} + . + 2 hk a^* b^* U^{12}]$

| | $U^{11}$ | $U^{22}$ | $U^{33}$ | $U^{23}$ | $U^{13}$ | $U^{12}$ |
|---|---|---|---|---|---|---|
| C(16) | 21(1) | 17(1) | 16(1) | −1(1) | 1(1) | 4(1) |
| C(17) | 25(1) | 24(1) | 16(1) | 4(1) | 3(1) | 4(1) |
| C(18) | 24(1) | 17(1) | 19(1) | 3(1) | 7(1) | 0(1) |
| C(19) | 22(1) | 31(1) | 23(1) | 1(1) | 10(1) | 4(1) |
| C(20A) | 42(2) | 18(1) | 24(2) | −5(1) | 18(1) | −4(1) |
| C(20B) | 46(5) | 34(6) | 23(5) | 13(4) | 10(3) | 19(4) |
| C(21) | 34(1) | 25(1) | 28(1) | −3(1) | 14(1) | 0(1) |
| O(7A) | 14(1) | 21(1) | 18(1) | 3(1) | 0(1) | −2(1) |
| C(22A) | 11(1) | 17(1) | 24(1) | 4(1) | −1(1) | 2(1) |
| C(23A) | 35(1) | 28(1) | 67(2) | −2(1) | 3(1) | −2(1) |
| O(7B) | 25(2) | 32(4) | 23(2) | 6(4) | −5(2) | 2(3) |
| C(22B) | 55(5) | 191(16) | 36(5) | −50(8) | 13(4) | −42(8) |
| C(23B) | 30(3) | 25(3) | 54(4) | 5(3) | 9(3) | 4(2) |
| O(8A) | 10(1) | 24(1) | 26(1) | 7(1) | 4(1) | 8(1) |
| C(24A) | 19(1) | 22(2) | 25(2) | 9(1) | 8(1) | 7(2) |
| O(8B) | 26(3) | 28(7) | 36(5) | 24(5) | 22(3) | 18(3) |
| C(24B) | 16(3) | 35(9) | 36(8) | 13(5) | 10(5) | 14(5) |
| C(25) | 20(1) | 36(1) | 29(1) | 11(1) | 3(1) | 9(1) |
| C(26) | 19(1) | 19(1) | 20(1) | −3(1) | 4(1) | −5(1) |

TABLE S5

Hydrogen coordinates ($\times 10^4$) and isotropic displacement
parameters ($Å^2 \times 10^3$)

| | x | y | z | U(eq) |
|---|---|---|---|---|
| H(8) | 5100 | 3931 | 6517 | 18 |
| H(9) | 4772 | 1086 | 6216 | 17 |
| H(13A) | 8908 | 1134 | 7326 | 39 |
| H(13B) | 8548 | −692 | 7065 | 39 |
| H(13C) | 8822 | 31 | 7219 | 51 |
| H(13D) | 8735 | 1929 | 7510 | 51 |
| H(15) | 6781 | −297 | 8613 | 27 |
| H(17A) | 4958 | 1043 | 8403 | 26 |
| H(17B) | 5315 | −825 | 8579 | 26 |
| H(18A) | 4682 | −1755 | 7405 | 24 |
| H(18B) | 4026 | −1091 | 7888 | 24 |
| H(19A) | 7125 | 2571 | 5650 | 37 |
| H(19B) | 6395 | 2304 | 4997 | 37 |
| H(19C) | 6810 | 698 | 5428 | 37 |
| H(20A) | 4372 | 4694 | 4884 | 32 |
| H(20B) | 3530 | 4311 | 4369 | 32 |
| H(20C) | 3310 | 3304 | 4204 | 41 |
| H(20D) | 3968 | 4642 | 4567 | 41 |
| H(21A) | 4626 | 3178 | 3826 | 42 |
| H(21B) | 4054 | 1669 | 4020 | 42 |
| H(21C) | 4890 | 2039 | 4537 | 42 |
| H(21D) | 4421 | 1412 | 4429 | 42 |
| H(21E) | 4993 | 2921 | 4235 | 42 |
| H(21F) | 4157 | 2551 | 3718 | 42 |
| H(22A) | 1061 | 3682 | 4548 | 21 |
| H(22B) | 1317 | 3174 | 5391 | 21 |
| H(23A) | 1988 | 1642 | 4223 | 66 |
| H(23B) | 1306 | 771 | 4620 | 66 |
| H(23C) | 2189 | 1093 | 5063 | 66 |
| H(22C) | 2065 | 1440 | 5324 | 112 |
| H(22D) | 1234 | 2489 | 5234 | 112 |
| H(23D) | 1148 | 2365 | 4004 | 54 |
| H(23E) | 1229 | 490 | 4339 | 54 |
| H(23F) | 1995 | 1390 | 4079 | 54 |
| H(24A) | 1786 | 7400 | 5168 | 26 |
| H(24B) | 1662 | 8592 | 5849 | 26 |
| H(24C) | 1689 | 6883 | 5022 | 34 |
| H(24D) | 1788 | 8224 | 5681 | 34 |
| H(25A) | 489 | 8679 | 4953 | 43 |
| H(25B) | 273 | 7859 | 5691 | 43 |
| H(25C) | 396 | 6666 | 5017 | 43 |
| H(25D) | 283 | 6790 | 5488 | 43 |
| H(25E) | 499 | 7611 | 4750 | 43 |
| H(25F) | 376 | 8803 | 5424 | 43 |
| H(26A) | 3915 | −1252 | 6274 | 29 |
| H(26B) | 3411 | 469 | 6121 | 29 |
| H(26C) | 3183 | −852 | 6714 | 29 |
| HN1 | 1937(11) | 6530(20) | 7378(10) | 39(3) |
| HN2 | 2775(11) | 6410(20) | 7888(11) | 39(3) |

Example 4

Baseline patients with food allergies treated with Tritoqualine alone or Montelukast alone (Singulair) did not yield satisfactory management of food allergy symptoms. The patients with food allergies described below demonstrate a synergic and surprising effect with the drug combination of Tritoqualine and Montelukast. Allergens tested came from either STALLERGENES, or ALLERBIO.

A pediatric patient had a history of anaphylaxis due to nut allergy (hazelnut/peanut) caused by ingestion of a hazelnut flavored cocoa spread marketed as "Nutella®". The direct test with the Nutella® was strongly positive for allergy. This patient was hospitalized in two occasions for the same dramatic allergic reaction to Nutella® spread. Furthermore, the patient presented allergies to pneumallergens.

The patient underwent anti-allergic treatment that did not modify his reaction to nut allergens. The second hospitalization occurred while the patient was under H1 antagonist and cromoglycate.

After treatment with the combination of Montelukast at the dose of 10 mg daily and Tritoqualine at the dose of 200 mg daily for a period of six weeks, it was possible to re-introduce the causal agent (Nutella® spread) to the patient without any major allergic reaction. Further, continuing the aforementioned treatment for six months the patient was able to eat more than 5 spoons of Nutella® spread without any noticeable allergic reaction. Digestive symptoms associated with this patient's allergy (stomach pain, diarrhea, constipation) completely disappeared after the treatment with the combination of Tritoqualine and Montelukast. Continuation of the above treatment for over 8 months afforded reversal of allergic and digestive symptoms due to food allergy.

Example 5

The patient under study had survived two cases of anaphylactic shock due to ingestion of shrimps. Each case of anaphylaxis resulted in hospitalization. Treatment with the combination of Tritoqualine 200 mg and Montelukast 10 mg for six weeks afforded gradual reintroduction of the allergenic food without symptoms of allergy. The first shrimp did not generate any local signs. Later the patient was able to ingest five shrimps without any local signs and no global reaction.

Example 6

Baseline patients had signs of food allergies and the food allergy symptoms were not adequately managed with an H1 antagonist and cromoglycate. A group of 15 patients presenting signs of food allergies is tested with allergens such as the following: peanut, milk, tomato, potato, flour of wheat, soybean, fish, and shrimp. Allergens tested came from either STALLERGENES, or ALLERBIO.

All patients had history of hospitalization and reactions such as Quincke's edema and asthma crisis. Most of the causal allergens were peanut (six patients), egg (four patients) and soybean (five patients) of them (with other several positive food allergens at different degrees of reaction). The patients presenting loco-regional reactions to food allergens after ingestion were treated with the combination of Tritoqualine and Montelukast.

Treatment with Tritoqualine 200 mg with 10 mg of Montelukast for 6 to 8 weeks afforded gradual reintroduction of the causal allergen without major allergic symptoms. One patient with a history of peanut allergy after 8 weeks of treatment presented a mild local reaction (itching of the lips). At 8 months of treatment the reintroduction of peanut did not cause local or general symptoms.

Example 7

In this study, the baseline patient was a 64 year old male with a COPD history. The COPD history of this patient extended 1 year of treatment prior to the initial visit (T0) and presented an average of eight hospitalization days per month due to complications of COPD.

At the initial visit to the physician (T0), the patient was examined and the spirometry parameter FEV1 was recorded. Tritoqualine 200 mg/day and Loratadine 10 mg/day were added to the patient's existing drug therapy. The patient had undergone physician examinations: 6 weeks, 6 months and 10 months after the start of the Tritoqualine/Loratadine treatment (T0). During each visit the patient's overall health and the FEV1 parameter was assessed by spirometry. Results from each visit are illustrated in Table 8.

TABLE 8

| Spirometry Parameter (L/s) | T0 (initial visit) | T2 (6 weeks) | T3 (6 months) | T4 (10 month) |
|---|---|---|---|---|
| FEV1 | 0.4 | 0.6 | 0.8 | 0.9 |
| FEV1 Normal value* | 3.2 | 3.2 | 3.2 | 3.2 |

*Normal Value is a value expected for healthy individuals based on age, and height During the period of treatment the patient showed improvement as evidenced by the fact that no hospitalization was necessary during the treatment period. Thus hospitalization decreased from an average of eight days per month to no hospitalization days at all. Further, the spirometry parameter FEV1 increased by 125% (from 0.4-0.9) during the 10 month treatment period, indicating improvement.

Therefore, the additional therapy, Tritoqualine 200 mg/day and Loratadine 10 mg/day ameliorated the COPD symptoms of the patient by significantly decreasing the frequency of hospitalization and improving the spirometry parameter FEV1 by 125% (0.5 L/s in 10 months).

Example 8

The baseline patient in this study was a 60 year old male with a COPD history that extended 2 years of treatment prior to the initial visit (T0).

At the initial visit to the physician (T0), the patient was examined and the spirometry parameter FEV1 was recorded. Tritoqualine 200 mg/day and Loratadine 10 mg/day were added to the patient's existing drug therapy. The patient had undergone physician examinations: 6 weeks, 6 months and 8 months after the start of the Tritoqualine/Loratadine treatment (T0). During each visit the patient's overall health and the FEV1 parameter was assessed by spirometry. Results from each visit are illustrated in Table 9.

TABLE 9

| Spirometry Parameter | T0 (initial visit) | T2 (6 weeks) | T3 (6 months) | T4 (8 month) |
|---|---|---|---|---|
| FEV1 (L/s) | 1.4 | 1.7 | 2.1 | 2.4 |
| FEV1 Normal value* (L/s) | 3.8 | 3.8 | 3.8 | 3.8 |

*Normal Value is a value expected for healthy individuals based on age, and height.

During the period of treatment the patient showed improvement as evidenced by an increase in the spirometry parameter FEV1, which increased by 71.4% (from 1.4-2.4) during the 8 month treatment period.

Therefore, the additional therapy, Tritoqualine 200 mg/day and Loratadine 10 mg/day, ameliorated the COPD symptoms of the patient by significantly improving the spirometry parameter FEV1 by 71.4% (1.0 L/s in 8 months).

Example 9

The baseline patient in this study was a 68 year old male with a COPD history that extended 3 years of treatment prior to the initial visit (T0).

At the initial visit to the physician (T0), the patient was examined and the spirometry parameter FEV1 was recorded. Tritoqualine 200 mg/day and Loratadine 10 mg/day were added to the patient's existing drug therapy. The patient had undergone physician examinations: 6 weeks, and 8 months after the start of the Tritoqualine/Loratadine treatment (T0). During each visit the patient's overall health and the FEV1 parameter was assessed by spirometry. Results from each visit are illustrated in Table 10.

TABLE 10

| Spirometry Parameter | T0 (initial visit) | T2 (6 weeks) | T3 (6 months) |
|---|---|---|---|
| FEV1 (L/s) | 1.2 | 1.8 | 1.9 |
| FEV1 Normal value* (L/s) | 3.8 | 3.8 | 3.8 |

*Normal Value is a value expected for healthy individuals based on age, and height.

During the period of treatment the patient showed improvement as evidenced by an increase in the spirometry parameter FEV1 increased by 58.3% (from 1.2-1.9) during the 8 month treatment period.

Therefore, the additional therapy, Tritoqualine 200 mg/day and Loratadine 10 mg/day, ameliorated the COPD symptoms of the patient by significantly improving the spirometry parameter FEV1 by 58.3% (0.7 L/s in 8 months).

Example 10

The baseline patient in this study was a 58 year old male with a COPD history that extended 3 years of treatment prior to the initial visit (T0).

At the initial visit to the physician (T0), the patient was examined and the spirometry parameter FEV1 was recorded. Tritoqualine 200 mg/day and Loratadine 10 mg/day were added to the patient's existing drug therapy. The patient had undergone physician examinations: 6 weeks, 6 months, and 12 months after the start of the Tritoqualine/Loratadine treatment (T0). During each visit the patient's overall health and the FEV1 parameter was assessed by spirometry. Results from each visit are illustrated in Table 11.

TABLE 11

| Spirometry Parameter | T0 (initial visit) | T2 (6 weeks) | T3 (6 months) | T4 (12 months) |
|---|---|---|---|---|
| FEV1 (L/s) | 1.8 | 2.1 | 2.1 | 2.6 |
| FEV1 Normal value* (L/s) | 3.1 | 3.1 | 3.1 | 3.1 |

*Normal Value is a value expected for healthy individuals based on age, and height.

During the period of treatment the patient showed improvement as evidenced by the increase in the spirometry parameter FEV1, which increased by 100.0% (from 1.8-2.6) during the 12 month treatment period.

Therefore, the additional therapy Tritoqualine 200 mg/day and Loratadine 10 mg/day ameliorated the COPD symptoms of the patient by significantly improving the spirometry parameter FEV1 by 44.4% (0.8 L/s in 12 months).

Example 11

The baseline patient in this study was a 67 year old male with a COPD history that extended 2 years of treatment prior to the initial visit (T0).

At the initial visit to the physician (T0), the patient was examined and the spirometry parameter FEV1 was recorded. Tritoqualine 200 mg/day and Loratadine 10 mg/day were added to the patient's existing drug therapy. The patient had undergone physician examinations: 8 weeks, 4 months, and 8 months after the start of the Tritoqualine/Loratadine treatment (T0). During each visit the patient's overall health and the FEV1 parameter was assessed by spirometry. Results from each visit are illustrated in Table 12.

TABLE 12

| Spirometry Parameter | T0 (initial visit) | T2 (6 weeks) | T3 (6 months) | T4 (12 months) |
|---|---|---|---|---|
| FEV1 (L/s) | 1.5 | 1.7 | 1.9 | 2.0 |
| FEV1 Normal value* (L/s) | 3.2 | 3.2 | 3.2 | 3.2 |

*Normal Value is a value expected for healthy individuals based on age, and height.

During the period of treatment the patient showed improvement as evidenced by the increase in the spirometry parameter FEV1, which increased by 100.0% (from 1.5-2.0) during the 8 month treatment period.

Therefore, the additional therapy, Tritoqualine 200 mg/day and Loratadine 10 mg/day, ameliorated the COPD symptoms of the patient by significantly improving the spirometry parameter FEV1 by 33.3% (0.5 L/s in 8 months).

The treatment with a combination of a histidine decarboxylase inhibitor such as Tritoqualine 200 mg/day and an anti-H1 drug such as Loratadine 10 mg/day dramatically ameliorated symptoms of COPD as shown by the respiratory parameter FEV1 and the decrease of the need of hospitalization.

What is claimed is:

1. A method for the treatment of gastroesophageal reflux disease in a subject, comprising administering to the subject ma effective amount of a composition consisting essentially of Tritoqualine or isomer thereof and pharmaceutically acceptable carriers, binders, diluents, adjuvants, excipients, and/or vehicles to the subject so as to treat gastroesophageal reflux disease in the subject.

2. The method of claim 1, wherein the effective amount of Tritoqualine is 200 mg/day.

3. The method of claim 1, wherein the subject is a mammal.

4. The method of claim 3, wherein the mammal is any of a human, monkey, ape, dog, cat, cow, horse, rabbit, mouse, or rat.

5. The method of claim 1, wherein the administration is effected orally, locally or systemically.

* * * * *